(12) United States Patent
Miraki

(10) Patent No.: US 11,395,650 B2
(45) Date of Patent: Jul. 26, 2022

(54) SYSTEMS FOR SECURING SUTURES

(71) Applicant: Edwards Lifesciences Corporation, Irvine, CA (US)

(72) Inventor: Manouchehr A. Miraki, Laguna Hills, CA (US)

(73) Assignee: Edwards Life Sciences Corporation, Irvine, CA (US)

( * ) Notice: Subject to any disclaimer, the term of this patent is extended or adjusted under 35 U.S.C. 154(b) by 26 days.

(21) Appl. No.: 17/008,619

(22) Filed: Aug. 31, 2020

(65) Prior Publication Data

US 2020/0390439 A1 Dec. 17, 2020

Related U.S. Application Data

(62) Division of application No. 14/773,129, filed as application No. PCT/US2015/032271 on May 22, 2015, now Pat. No. 10,786,244.

(Continued)

(51) Int. Cl.
*A61B 17/04* (2006.01)
*A61B 1/05* (2006.01)
(Continued)

(52) U.S. Cl.
CPC ............ *A61B 17/0487* (2013.01); *A61B 1/05* (2013.01); *A61B 1/0676* (2013.01);
(Continued)

(58) Field of Classification Search
CPC ............ A61B 17/0469; A61B 17/0487; A61B 17/128; A61B 17/1285;
(Continued)

(56) References Cited

U.S. PATENT DOCUMENTS 1,358,477 A 11/1920 Stout
2,264,679 A 12/1941 Ravel
(Continued)

FOREIGN PATENT DOCUMENTS

CA 2141911 4/2002
CA 2141913 4/2002
(Continued)

OTHER PUBLICATIONS

LSI Solutions T-Knot Device 2, LSI Solutions, Inc., 2009-2011, http://www.lsisolutions.com/tkoutsideofcannuia.
(Continued)

*Primary Examiner* — Wade Miles
*Assistant Examiner* — Kankindi Rwego
(74) *Attorney, Agent, or Firm* — Klarquist Sparkman, LLP

(57) ABSTRACT

Described herein are systems and methods for securing sutures that obviate the need for tying knots. Disclosed suture clips can comprise a first part and a second part that are attachable together to secure one or more sutures in a suture engagement region between the first and second parts. The first and second parts can include locking projections and slots at opposing ends of the suture engagement region to align the two parts, contain sutures, and/or secure the clip onto sutures. When the first and second parts are attached together, first engagement features of the first part interengage with second engagement features of the second part to grip and secure sutures within suture engagement region. An exemplary delivery device holds a plurality of such suture clips in an elongated shaft portion and deploys the clips successively to sutures via actuation of a handle portion.

20 Claims, 13 Drawing Sheets

Related U.S. Application Data

(60) Provisional application No. 62/005,517, filed on May 30, 2014.

(51) Int. Cl.

| | | |
|---|---|---|
| *A61B 1/06* | (2006.01) | |
| *A61B 17/00* | (2006.01) | |
| *A61B 17/29* | (2006.01) | |
| *A61B 90/30* | (2016.01) | |
| *A61B 90/00* | (2016.01) | |
| *A61B 17/30* | (2006.01) | |

(52) U.S. Cl.
CPC .......... *A61B 17/0469* (2013.01); *A61B 90/30* (2016.02); *A61B 90/361* (2016.02); *A61B 2017/003* (2013.01); *A61B 2017/00243* (2013.01); *A61B 2017/00296* (2013.01); *A61B 2017/00407* (2013.01); *A61B 2017/00477* (2013.01); *A61B 2017/00946* (2013.01); *A61B 2017/0488* (2013.01); *A61B 2017/2905* (2013.01); *A61B 2017/306* (2013.01)

(58) Field of Classification Search
CPC .......... A61B 2017/00243; A61B 2017/00296; A61B 2017/003; A61B 2017/00407; A61B 2017/00477; A61B 2017/00946; A61B 2017/0488; A61B 2017/2905; A61B 2017/306; A61B 1/05; A61B 1/0676; A61B 90/30; A61B 90/361; A61F 2/2427
USPC ...................................................... 606/232
See application file for complete search history.

(56) References Cited

U.S. PATENT DOCUMENTS

| | | |
|---|---|---|
| 2,516,710 A | 7/1950 | Mascolo |
| 2,715,486 A | 8/1955 | Marcoff-Moghadam et al. |
| 2,890,519 A | 6/1959 | Storz, Jr. |
| 2,981,990 A | 5/1961 | Baiderree, Jr. |
| 3,143,742 A | 8/1964 | Cromie |
| 3,249,104 A | 5/1966 | Hohnstein |
| 3,274,658 A | 9/1966 | Pile |
| 3,452,742 A | 7/1969 | Muller |
| 3,506,012 A | 4/1970 | Brown |
| 3,509,882 A | 5/1970 | Blake |
| 3,541,591 A | 11/1970 | Hoegerman |
| 3,547,103 A | 12/1970 | Cook |
| 3,570,497 A | 3/1971 | Lemole |
| 3,608,095 A | 9/1971 | Barry |
| 3,638,654 A | 2/1972 | Akuba |
| RE27,391 E | 6/1972 | Merser |
| 3,753,438 A | 8/1973 | Wood et al. |
| 3,859,668 A | 1/1975 | Anderson |
| 3,875,648 A | 4/1975 | Bone |
| 3,898,999 A | 8/1975 | Haller |
| 3,910,281 A | 10/1975 | Kletschka et al. |
| 3,954,108 A | 5/1976 | Davis |
| 3,954,109 A | 5/1976 | Patel |
| 3,958,576 A | 5/1976 | Komiya |
| 3,976,079 A | 8/1976 | Samuels et al. |
| 3,988,810 A | 11/1976 | Emery |
| 3,996,623 A | 12/1976 | Kaster |
| 4,038,725 A | 8/1977 | Keefe |
| 4,103,690 A | 8/1978 | Harris |
| 4,140,125 A | 2/1979 | Smith |
| 4,170,990 A | 10/1979 | Baumgart et al. |
| 4,192,315 A | 3/1980 | Hilzinger et al. |
| 4,217,902 A | 8/1980 | March |
| 4,324,248 A | 4/1982 | Perlin |
| 4,345,601 A | 8/1982 | Fukuda |
| 4,416,266 A | 11/1983 | Baucom |
| 4,456,017 A | 6/1984 | Miles |
| 4,485,816 A | 12/1984 | Krumme |
| 4,522,207 A | 6/1985 | Klieman et al. |
| 4,535,764 A | 8/1985 | Ebert |
| 4,548,202 A | 10/1985 | Duncan |
| 4,549,545 A | 10/1985 | Levy |
| 4,570,304 A | 2/1986 | Montreuil et al. |
| 4,586,502 A | 5/1986 | Bedi et al. |
| 4,586,503 A | 5/1986 | Kirsch et al. |
| 4,595,007 A | 6/1986 | Mericle |
| 4,612,932 A | 9/1986 | Caspar et al. |
| 4,637,380 A | 1/1987 | Orejola |
| 4,665,906 A | 5/1987 | Jervis |
| 4,683,895 A | 8/1987 | Pohndorf |
| 4,705,040 A | 11/1987 | Mueller et al. |
| 4,719,924 A | 1/1988 | Crittenden et al. |
| 4,730,615 A | 3/1988 | Sutherland et al. |
| 4,741,330 A | 5/1988 | Hayhurst |
| 4,743,253 A | 5/1988 | Magladry |
| 4,750,492 A | 6/1988 | Jacobs |
| 4,809,695 A | 3/1989 | Gwathmey et al. |
| 4,823,794 A | 4/1989 | Pierce |
| 4,863,460 A | 9/1989 | Magladry |
| 4,873,975 A | 10/1989 | Walsh et al. |
| 4,896,668 A | 1/1990 | Popoff et al. |
| 4,899,744 A | 2/1990 | Fujitsuka et al. |
| 4,901,721 A | 2/1990 | Hakki |
| 4,914,789 A | 4/1990 | Pedersen |
| 4,924,866 A | 5/1990 | Yoon |
| 4,926,860 A | 5/1990 | Stice et al. |
| 4,929,240 A | 5/1990 | Kirsch et al. |
| 4,932,955 A | 6/1990 | Merz et al. |
| 4,950,283 A | 8/1990 | Dzubow et al. |
| 4,950,285 A | 8/1990 | Wilk |
| 4,955,913 A | 9/1990 | Robinson |
| 4,976,715 A | 12/1990 | Bays et al. |
| 4,983,176 A | 1/1991 | Cushman et al. |
| 4,990,152 A | 2/1991 | Yoon |
| 4,997,439 A | 3/1991 | Chen |
| 5,002,550 A | 3/1991 | Li |
| 5,002,562 A | 3/1991 | Oberlander |
| 5,002,563 A | 3/1991 | Pyka et al. |
| 5,026,379 A | 6/1991 | Yoon |
| 5,047,047 A | 9/1991 | Yoon |
| 5,053,047 A | 10/1991 | Yoon |
| 5,070,805 A | 12/1991 | Plante |
| 5,071,431 A | 12/1991 | Sauter et al. |
| 5,074,874 A | 12/1991 | Yoon et al. |
| 5,078,731 A | 1/1992 | Hayhurst |
| 5,100,418 A | 3/1992 | Yoon et al. |
| 5,116,840 A | 5/1992 | Ganguly et al. |
| 5,123,913 A | 6/1992 | Wilk |
| RE34,021 E | 8/1992 | Mueller et al. |
| 5,152,769 A | 10/1992 | Baber |
| 5,154,189 A | 10/1992 | Oberiander |
| 5,158,566 A | 10/1992 | Pianetti |
| 5,163,954 A | 11/1992 | Curcio et al. |
| 5,171,250 A | 12/1992 | Yoon |
| 5,171,251 A | 12/1992 | Bregen et al. |
| 5,171,252 A | 12/1992 | Friedland |
| 5,174,087 A | 12/1992 | Bruno |
| 5,196,022 A | 3/1993 | Bilweis |
| 5,219,358 A | 6/1993 | Bendel et al. |
| 5,222,976 A | 6/1993 | Yoon |
| 5,231,735 A | 8/1993 | Paxton |
| 5,234,449 A | 8/1993 | Bruker et al. |
| 5,236,440 A | 8/1993 | Hlavacek |
| 5,242,456 A | 9/1993 | Nash et al. |
| 5,246,443 A | 9/1993 | Mai |
| 5,258,011 A | 11/1993 | Drews |
| 5,258,015 A | 11/1993 | Li et al. |
| 5,269,783 A | 12/1993 | Sander |
| 5,269,809 A | 12/1993 | Hayhurst et al. |
| 5,282,832 A | 2/1994 | Toso et al. |
| 5,290,289 A | 3/1994 | Sanders et al. |
| 5,304,204 A | 4/1994 | Bregen |
| 5,306,290 A | 4/1994 | Martins et al. |
| 5,306,296 A | 4/1994 | Wright et al. |
| 5,312,423 A | 5/1994 | Rosenbluth et al. |
| 5,312,436 A | 5/1994 | Coffey et al. |
| 5,330,442 A | 7/1994 | Green et al. |

(56) References Cited

U.S. PATENT DOCUMENTS

| | | |
|---|---|---|
| 5,330,503 A | 7/1994 | Yoon |
| 5,336,239 A | 8/1994 | Gimpelson |
| 5,356,424 A | 10/1994 | Buzerak et al. |
| 5,374,268 A | 12/1994 | Sander |
| 5,381,588 A | 1/1995 | Nelson |
| 5,383,904 A | 1/1995 | Totakura et al. |
| 5,383,905 A | 1/1995 | Golds et al. |
| 5,391,173 A | 2/1995 | Wilk |
| 5,403,346 A | 4/1995 | Loeser |
| 5,409,499 A | 4/1995 | Yi |
| 5,437,680 A | 8/1995 | Yoon |
| 5,437,685 A | 8/1995 | Blasnik |
| 5,439,479 A | 8/1995 | Shichman et al. |
| 5,445,167 A | 8/1995 | Yoon et al. |
| 5,450,860 A | 9/1995 | O'Connor |
| 5,452,733 A | 9/1995 | Sterman et al. |
| 5,456,246 A | 10/1995 | Schmieding et al. |
| 5,462,561 A | 10/1995 | Voda |
| 5,474,557 A | 12/1995 | Mai |
| 5,474,572 A | 12/1995 | Hayhurst |
| 5,480,405 A | 1/1996 | Yoon |
| 5,486,197 A | 1/1996 | Le et al. |
| 5,496,336 A | 3/1996 | Cosgrove et al. |
| 5,499,990 A | 3/1996 | Schulken et al. |
| 5,500,000 A | 3/1996 | Feagin et al. |
| 5,520,691 A | 5/1996 | Branch |
| 5,520,702 A | 5/1996 | Sauer et al. |
| 5,527,342 A | 6/1996 | Pietrzak et al. |
| 5,531,763 A | 7/1996 | Mastri et al. |
| 5,545,178 A | 8/1996 | Kensey et al. |
| 5,549,619 A | 8/1996 | Peters et al. |
| 5,562,685 A | 10/1996 | Mollenauer et al. |
| 5,569,274 A | 10/1996 | Rapacki et al. |
| 5,569,301 A | 10/1996 | Granger et al. |
| 5,573,543 A | 11/1996 | Akopov et al. |
| 5,582,616 A | 12/1996 | Bolduc et al. |
| 5,582,619 A | 12/1996 | Ken |
| 5,586,983 A | 12/1996 | Sanders et al. |
| 5,591,179 A | 1/1997 | Edelstein |
| 5,593,414 A | 1/1997 | Shipp et al. |
| 5,593,424 A | 1/1997 | Northrup, III |
| 5,609,608 A | 3/1997 | Benett et al. |
| 5,626,590 A | 5/1997 | Wilk |
| 5,630,824 A | 5/1997 | Hart |
| 5,632,752 A | 5/1997 | Buelna |
| 5,632,753 A | 5/1997 | Loeser |
| 5,643,289 A | 7/1997 | Sauer et al. |
| 5,643,295 A | 7/1997 | Yoon |
| 5,645,553 A | 7/1997 | Kolesa et al. |
| 5,645,568 A | 7/1997 | Chervitz et al. |
| 5,665,109 A | 9/1997 | Yoon |
| 5,669,917 A | 9/1997 | Sauer et al. |
| 5,669,935 A | 9/1997 | Rosenman et al. |
| 5,681,351 A | 10/1997 | Jamiolkowski et al. |
| 5,683,417 A | 11/1997 | Cooper |
| 5,695,505 A | 12/1997 | Yoon |
| 5,697,943 A | 12/1997 | Sauer et al. |
| 5,700,270 A | 12/1997 | Peyser et al. |
| 5,700,271 A | 12/1997 | Whitfield |
| 5,707,380 A | 1/1998 | Hinchliffe et al. |
| 5,709,693 A | 1/1998 | Taylor |
| 5,709,695 A | 1/1998 | Northrup, III |
| 5,725,539 A | 3/1998 | Matern |
| 5,725,542 A | 3/1998 | Yoon |
| 5,725,556 A | 3/1998 | Moser et al. |
| 5,728,135 A | 3/1998 | Bregen et al. |
| 5,735,290 A | 4/1998 | Sterman et al. |
| 5,735,877 A | 4/1998 | Pagedas |
| 5,766,183 A | 6/1998 | Sauer |
| 5,776,188 A | 7/1998 | Shepherd et al. |
| 5,799,661 A | 9/1998 | Boyd et al. |
| 5,810,851 A | 9/1998 | Yoon |
| 5,810,882 A | 9/1998 | Bolduc et al. |
| 5,820,631 A | 10/1998 | Nobles |
| 5,824,008 A | 10/1998 | Bolduc et al. |
| 5,830,221 A | 11/1998 | Stein et al. |
| 5,833,696 A | 11/1998 | Whitfield et al. |
| 5,845,645 A | 12/1998 | Bonutti |
| 5,849,019 A | 12/1998 | Yoon |
| 5,852,851 A | 12/1998 | Cooper |
| 5,861,004 A | 1/1999 | Kensey et al. |
| 5,879,371 A | 3/1999 | Gardiner et al. |
| 5,891,130 A | 4/1999 | Palermo et al. |
| 5,891,160 A | 4/1999 | Williamson, IV et al. |
| 5,895,393 A | 4/1999 | Pagedas |
| 5,895,394 A | 4/1999 | Kienzle et al. |
| 5,919,207 A | 7/1999 | Taheri |
| 5,948,001 A | 9/1999 | Larsen |
| 5,961,481 A | 10/1999 | Sterman et al. |
| 5,961,539 A | 10/1999 | Northrup, III et al. |
| 5,964,772 A | 10/1999 | Bolduc et al. |
| 5,972,024 A | 10/1999 | Northrup, III et al. |
| 5,976,159 A | 11/1999 | Bolduc et al. |
| 5,984,917 A | 11/1999 | Fleischman et al. |
| 5,989,242 A | 11/1999 | Saadat et al. |
| 5,989,268 A | 11/1999 | Pugsley, Jr. et al. |
| 5,997,556 A | 12/1999 | Tanner |
| 6,001,110 A | 12/1999 | Adams |
| 6,013,084 A | 1/2000 | Ken et al. |
| 6,015,428 A | 1/2000 | Pagedas |
| 6,039,176 A | 3/2000 | Wright |
| 6,066,160 A | 5/2000 | Colvin |
| 6,074,409 A | 6/2000 | Goldfarb |
| 6,120,524 A | 9/2000 | Taheri |
| 6,132,438 A | 10/2000 | Fleischman et al. |
| 6,139,540 A | 10/2000 | Rost et al. |
| 6,143,004 A | 11/2000 | Davis et al. |
| 6,176,413 B1 | 1/2001 | Heck et al. |
| 6,190,373 B1 | 2/2001 | Palermo et al. |
| 6,193,733 B1 | 2/2001 | Adams |
| 6,193,734 B1 | 2/2001 | Bolduc et al. |
| 6,231,592 B1 | 5/2001 | Bonutti et al. |
| 6,241,765 B1 | 6/2001 | Griffin et al. |
| 6,254,615 B1 | 7/2001 | Bolduc et al. |
| 6,306,141 B1 | 10/2001 | Jervis |
| 6,346,112 B2 | 2/2002 | Adams |
| 6,368,334 B1 | 4/2002 | Sauer |
| 6,432,123 B2 | 8/2002 | Schwartz et al. |
| 6,475,230 B1 | 11/2002 | Bonutti et al. |
| 6,514,265 B2 | 2/2003 | Ho et al. |
| 6,533,796 B1 | 3/2003 | Sauer et al. |
| 6,537,290 B2 | 3/2003 | Adams et al. |
| 6,551,332 B1 | 4/2003 | Nguyen et al. |
| 6,589,279 B1 | 7/2003 | Anderson et al. |
| 6,607,541 B1 | 8/2003 | Gardiner et al. |
| 6,613,059 B2 | 9/2003 | Schaller et al. |
| 6,626,930 B1 | 9/2003 | Allen et al. |
| 6,641,592 B1 | 11/2003 | Sauer et al. |
| 6,641,593 B1 | 11/2003 | Schaller et al. |
| 6,682,540 B1 | 1/2004 | Sancoff et al. |
| 6,719,767 B1 | 4/2004 | Kimblad |
| 6,743,239 B1 * | 6/2004 | Kuehn ............... A61B 17/0643 |
| | | 464/149 |
| 6,746,457 B2 | 6/2004 | Dana et al. |
| 6,749,622 B2 | 6/2004 | McGuckin, Jr. et al. |
| 6,776,784 B2 | 8/2004 | Ginn |
| 6,860,890 B2 | 3/2005 | Bachman et al. |
| 6,896,686 B2 | 5/2005 | Weber |
| 6,913,607 B2 | 7/2005 | Ainsworth et al. |
| 6,918,917 B1 | 7/2005 | Nguyen et al. |
| 6,921,407 B2 | 7/2005 | Nguyen et al. |
| 6,926,730 B1 | 8/2005 | Nguyen et al. |
| 6,945,980 B2 | 9/2005 | Nguyen et al. |
| 6,960,221 B2 | 11/2005 | Ho et al. |
| 7,011,669 B2 | 3/2006 | Kimblad |
| 7,083,628 B2 | 8/2006 | Bachman |
| 7,094,244 B2 | 8/2006 | Schreck |
| 7,112,207 B2 | 9/2006 | Allen et al. |
| 7,220,266 B2 | 5/2007 | Gambale |
| 7,235,086 B2 | 6/2007 | Sauer et al. |
| 7,264,625 B1 | 9/2007 | Buncke |
| 7,381,210 B2 | 6/2008 | Zarbatany et al. |
| 7,628,797 B2 | 12/2009 | Tieu et al. |
| 7,677,525 B2 | 3/2010 | Sanchez et al. |

(56) References Cited

U.S. PATENT DOCUMENTS

| | | | |
|---|---|---|---|
| 7,731,727 B2 | 6/2010 | Sauer | |
| 7,833,237 B2 | 11/2010 | Sauer | |
| 7,842,051 B2 | 11/2010 | Dana et al. | |
| 7,862,548 B2 | 1/2011 | Javer et al. | |
| 7,862,584 B2 | 1/2011 | Lyons et al. | |
| 7,875,056 B2 | 1/2011 | Jervis et al. | |
| 7,959,674 B2 | 6/2011 | Shu et al. | |
| 7,981,139 B2 | 7/2011 | Martin et al. | |
| 8,021,421 B2 | 9/2011 | Fogarty et al. | |
| 8,100,923 B2 | 1/2012 | Paraschac et al. | |
| 8,105,355 B2 | 1/2012 | Page et al. | |
| 8,252,005 B2 | 8/2012 | Findlay, III et al. | |
| 8,398,657 B2 | 3/2013 | Sauer | |
| 8,398,680 B2 | 3/2013 | Sauer et al. | |
| 8,425,555 B2 | 4/2013 | Page et al. | |
| 8,465,505 B2 | 6/2013 | Murillo et al. | |
| 8,480,686 B2 | 7/2013 | Bakos et al. | |
| 8,753,373 B2 | 6/2014 | Chau et al. | |
| 9,017,347 B2 | 4/2015 | Oba et al. | |
| 10,786,244 B2* | 9/2020 | Miraki | A61B 1/05 |
| 2001/0025181 A1 | 9/2001 | Freedlan | |
| 2002/0029060 A1 | 3/2002 | Hogendijk | |
| 2003/0009196 A1 | 1/2003 | Peterson | |
| 2003/0109922 A1 | 6/2003 | Peterson et al. | |
| 2003/0167062 A1* | 9/2003 | Gambale | A61B 17/0487 606/138 |
| 2003/0195563 A1 | 10/2003 | Foerster | |
| 2003/0233105 A1 | 12/2003 | Gayton | |
| 2004/0181238 A1 | 9/2004 | Zarbatany et al. | |
| 2004/0204724 A1 | 10/2004 | Kissel et al. | |
| 2004/0249414 A1 | 12/2004 | Kissel et al. | |
| 2005/0096699 A1* | 5/2005 | Wixey | A61B 17/0487 606/232 |
| 2005/0251206 A1 | 11/2005 | Maahs et al. | |
| 2005/0251209 A1 | 11/2005 | Saadat et al. | |
| 2006/0047314 A1 | 3/2006 | Green | |
| 2006/0079913 A1 | 4/2006 | Whitfield et al. | |
| 2006/0089571 A1 | 4/2006 | Gertner | |
| 2006/0184203 A1 | 8/2006 | Martin et al. | |
| 2006/0265010 A1 | 11/2006 | Paraschac et al. | |
| 2006/0276871 A1 | 12/2006 | Lamson et al. | |
| 2006/0282119 A1 | 12/2006 | Perchik | |
| 2007/0005079 A1 | 1/2007 | Zarbatany et al. | |
| 2007/0005081 A1 | 1/2007 | Findlay et al. | |
| 2007/0049952 A1 | 3/2007 | Weiss | |
| 2007/0049970 A1 | 3/2007 | Belef et al. | |
| 2007/0088391 A1 | 4/2007 | McAlexander et al. | |
| 2007/0179530 A1 | 8/2007 | Tieu et al. | |
| 2007/0255296 A1 | 11/2007 | Sauer | |
| 2007/0270907 A1 | 11/2007 | Stokes et al. | |
| 2008/0154286 A1 | 6/2008 | Abbott et al. | |
| 2008/0255591 A1 | 10/2008 | Harada et al. | |
| 2008/0281356 A1 | 11/2008 | Chau et al. | |
| 2009/0143821 A1 | 6/2009 | Stupak | |
| 2009/0281377 A1 | 11/2009 | Newell et al. | |
| 2009/0281568 A1 | 11/2009 | Cendan et al. | |
| 2010/0001038 A1 | 1/2010 | Levin et al. | |
| 2010/0076462 A1 | 3/2010 | Bakos et al. | |
| 2010/0324597 A1 | 12/2010 | Shikhman | |
| 2010/0324598 A1 | 12/2010 | Anderson | |
| 2011/0087241 A1 | 4/2011 | Nguyen | |
| 2011/0087242 A1 | 4/2011 | Pribanic et al. | |
| 2011/0224485 A1 | 9/2011 | Boulnois et al. | |
| 2011/0224714 A1 | 9/2011 | Gertner | |
| 2011/0283514 A1 | 11/2011 | Fogarty et al. | |
| 2012/0080495 A1 | 4/2012 | Holcomb et al. | |
| 2012/0089182 A1 | 4/2012 | Page et al. | |
| 2012/0101526 A1 | 4/2012 | Bennett | |
| 2012/0102526 A1 | 4/2012 | Lejeune | |
| 2013/0110164 A1 | 5/2013 | Milazzo et al. | |
| 2013/0158600 A1 | 6/2013 | Conklin et al. | |
| 2013/0267998 A1 | 10/2013 | Vijay et al. | |
| 2013/0282028 A1 | 10/2013 | Conklin et al. | |
| 2014/0031864 A1 | 1/2014 | Jafari et al. | |

FOREIGN PATENT DOCUMENTS

| | | |
|---|---|---|
| CN | 2558335 Y | 7/2003 |
| CN | 102400298 A | 4/2012 |
| DE | 69512446 T2 | 5/2000 |
| DE | 69612447 T2 | 7/2001 |
| EP | 0669101 A1 | 8/1995 |
| EP | 0669103 A1 | 8/1995 |
| EP | 1484023 A1 | 12/2004 |
| EP | 2260774 A2 | 12/2010 |
| WO | 0030550 A1 | 6/2000 |
| WO | 01049207 A2 | 7/2001 |
| WO | 0166001 A2 | 9/2001 |

OTHER PUBLICATIONS

LSI Solutions T-Knot Device, LSI Solutions, Inc., 2009-2011, http://www.Isisolutions.com/tkatscrubtable.

TK Quick Load, LSI Solutions, http://www.Isisolutions.com/tkquickload.

* cited by examiner

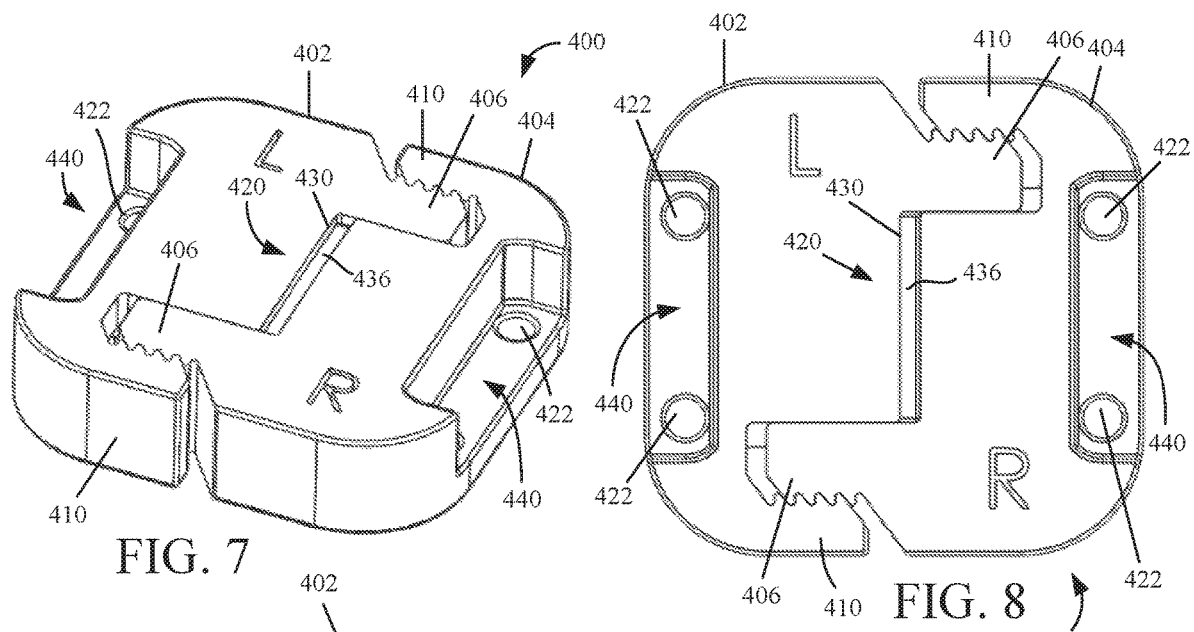
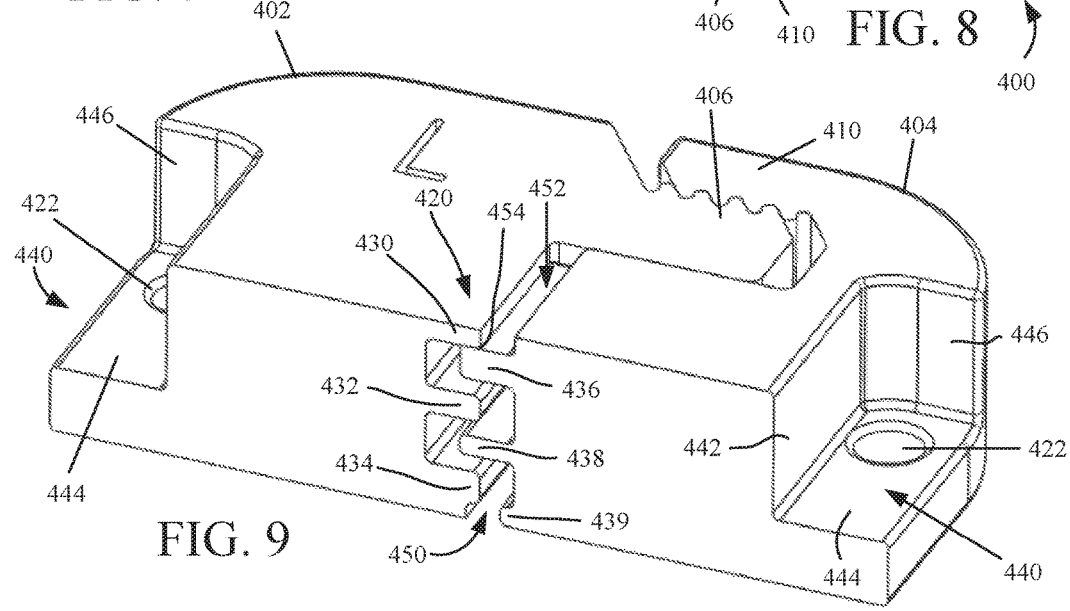
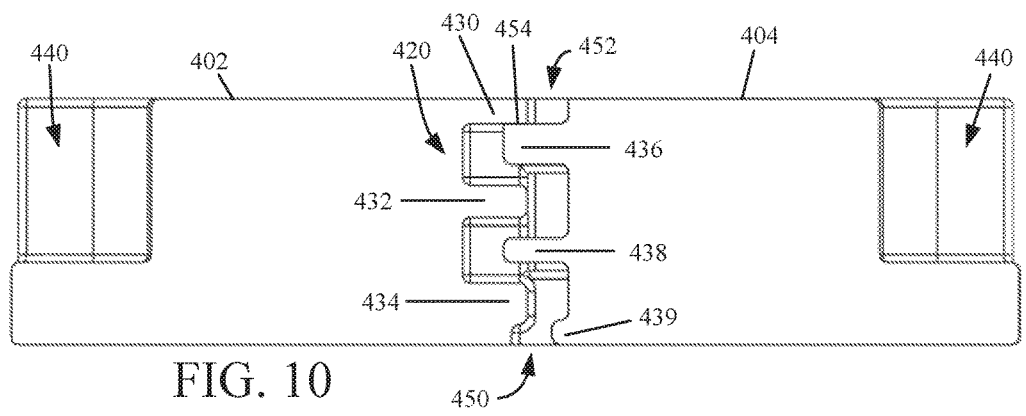

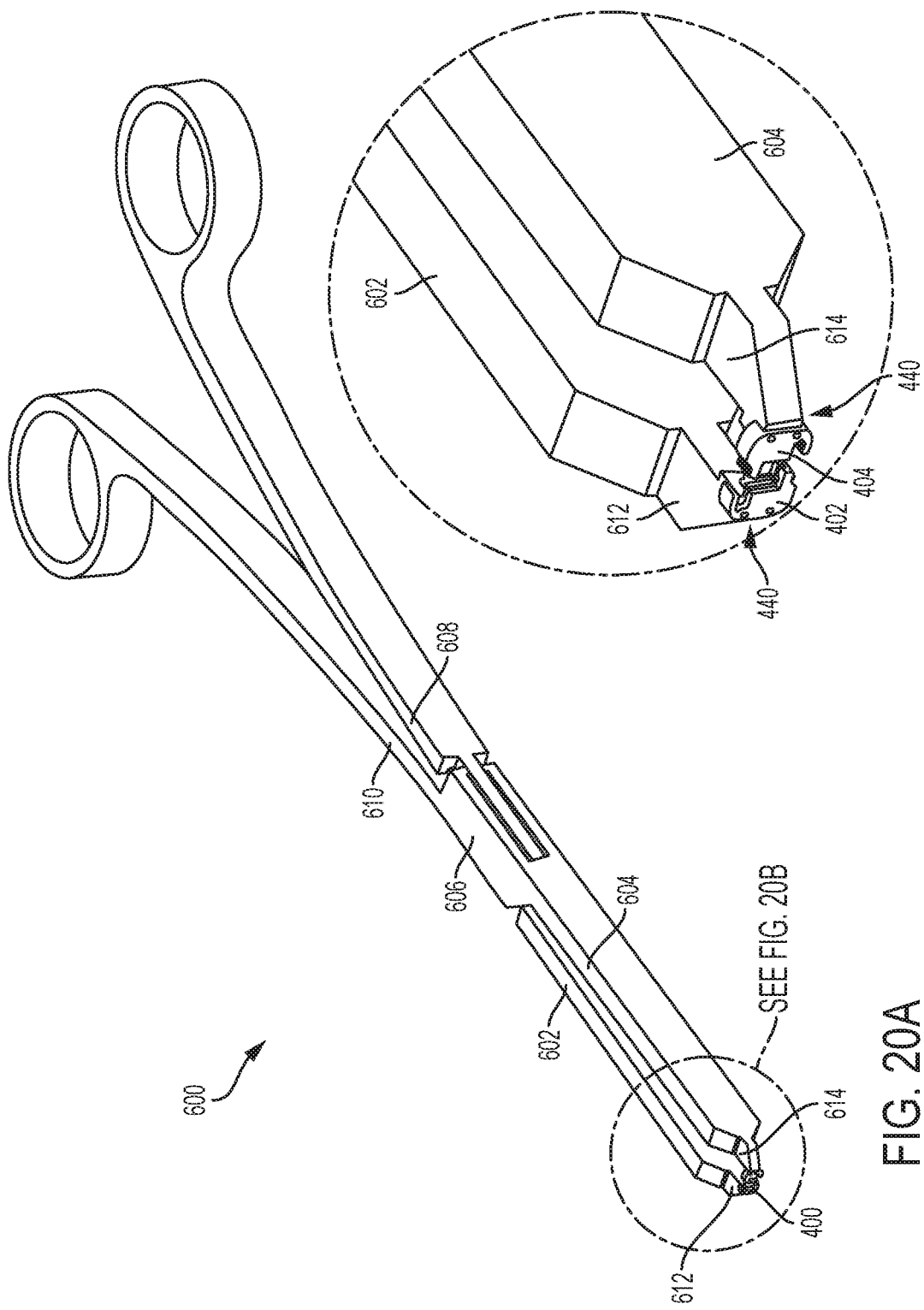

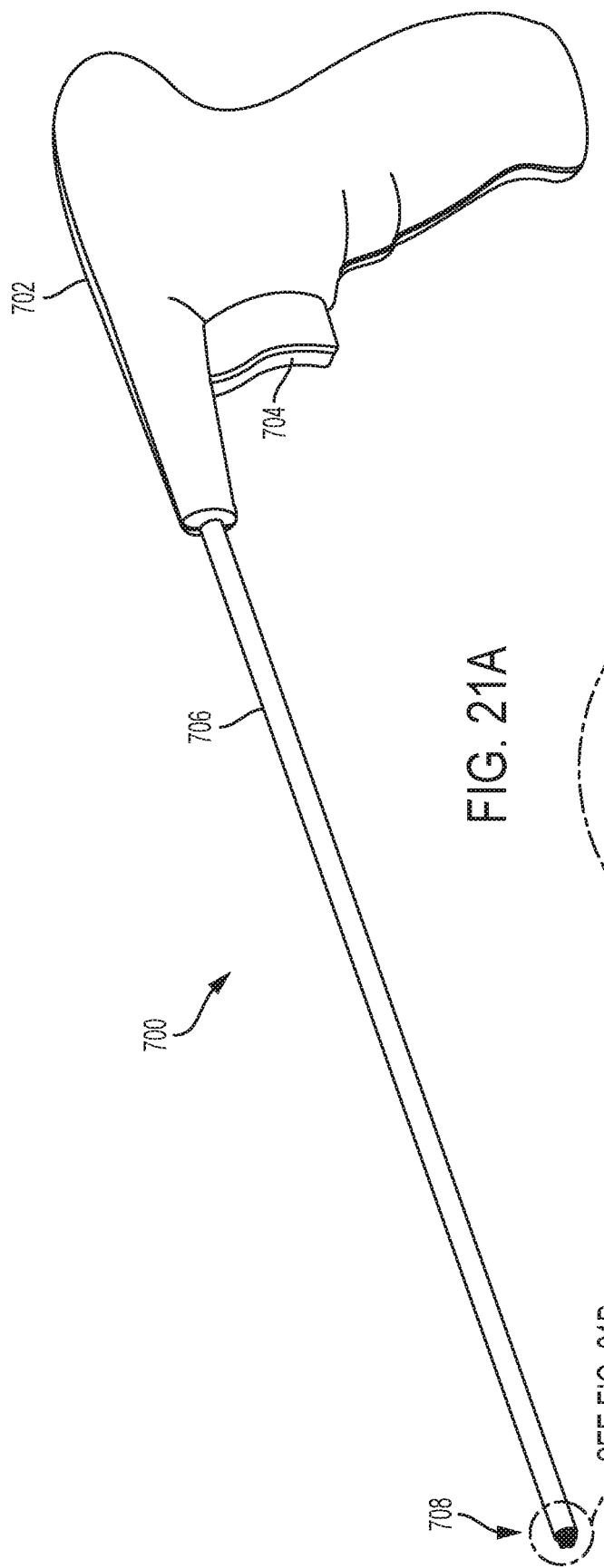
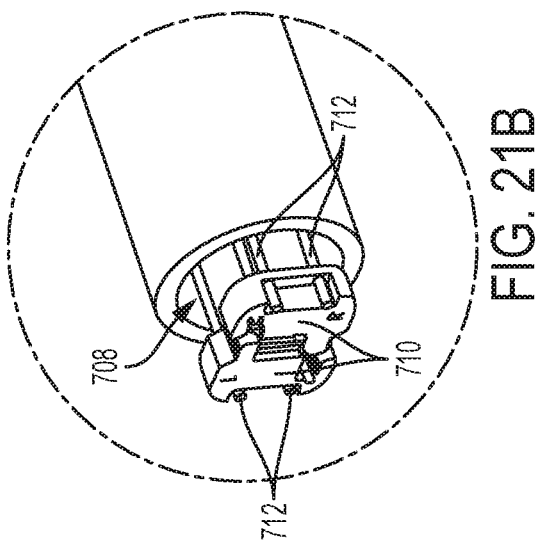
FIG. 21A
FIG. 21B

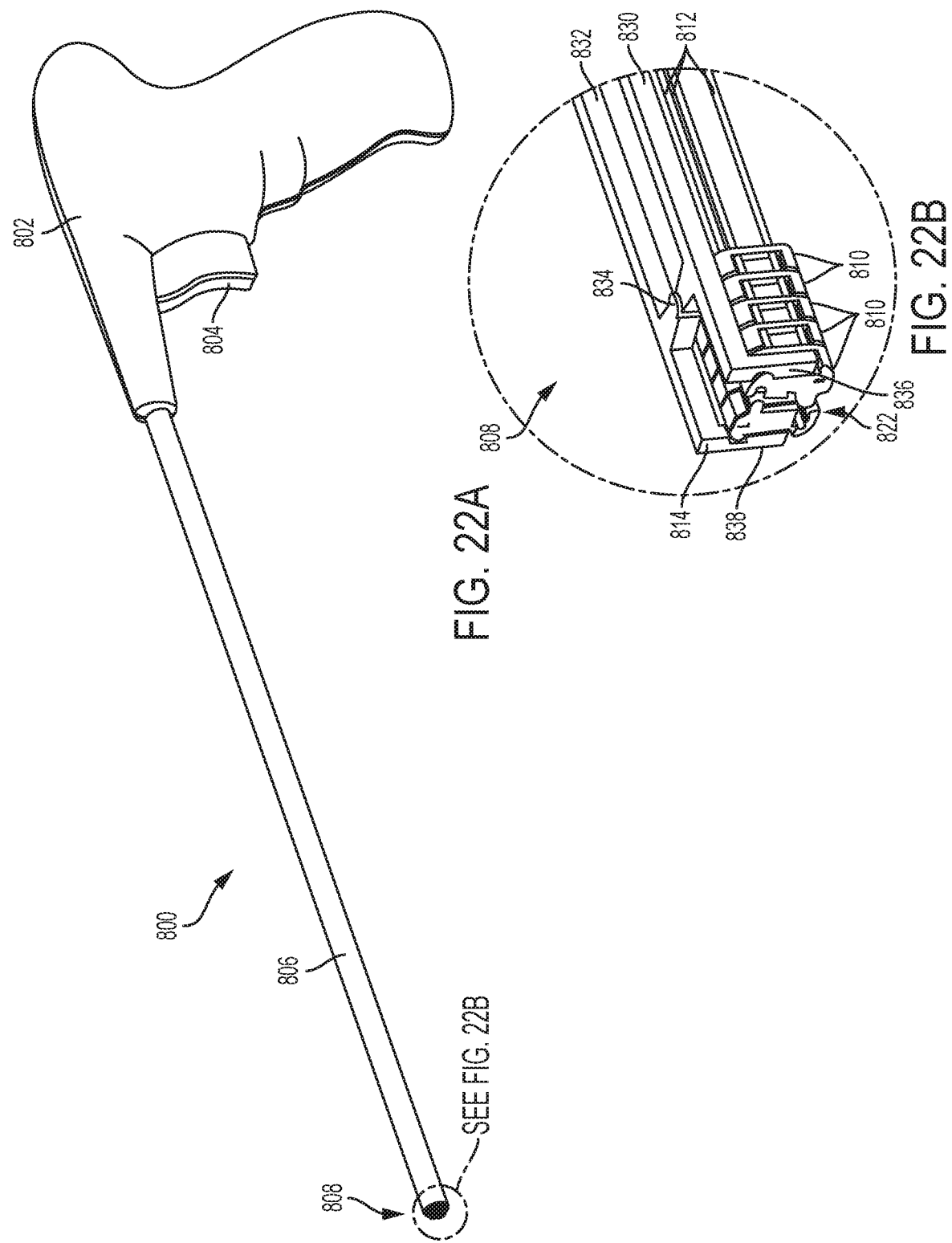

SYSTEMS FOR SECURING SUTURES

CROSS-REFERENCE TO RELATED APPLICATIONS

This application is a divisional of U.S. patent application Ser. No. 14/773,129, filed Mar. 18, 2016, which is the U.S. National Stage of International Application No. PCT/US2015/32271, filed May 22, 2015, which claims the benefit of U.S. Patent Application No. 62/005,517, filed May 30, 2014, all of which are incorporated by reference herein in their entirety.

FIELD

This disclosure is related to devices and methods for securing surgical sutures.

BACKGROUND

Surgically placed sutures are frequently used in many different surgical procedures. Exemplary procedures include implantation of a prosthetic device within the heart and closing an open section of blood vessel to secure placement of tubes for cardiopulmonary bypass. In such procedures, different suture types and suture patterns are often used, such as purse string sutures, mattress sutures, running sutures, and others. Conventionally, at the end of such a procedure, the two free ends of each suture are tied together in a knot to secure the suture in place.

SUMMARY

Described herein are devices, systems, and methods for securing sutures that obviate the need for tying knots. For example, disclosed suture clips can comprise a first part and a second part that are attachable together to secure one or more sutures in a suture engagement region between the first and second parts. The first and second parts can include locking projections and corresponding slots at opposing ends of the suture engagement region to align the two parts, contain sutures, and/or secure the clip onto sutures. When the first and second parts are attached together, first engagement features of the first part inter-engage with second engagement features of the second part to grip and secure sutures within the suture engagement region. Exemplary delivery devices are also disclosed, such as embodiments that can hold a plurality of such suture clips in an elongated shaft portion and deploy the clips successively to sutures via actuation of a handle portion.

In some suture clip embodiments, a first locking projection in a first part of the clip comprises a first plurality of teeth and a corresponding locking slot in the second part of the clip comprises a second plurality of teeth, and first and second pluralities of teeth engage with each other as the first locking projection moves into the corresponding locking slot to prevent the first and second parts from separating.

In some suture clip embodiments, a first projection in the first clip part comprises a first alignment feature and a corresponding slot in the second clip part comprises a second alignment feature, such that the first and second alignment features engage with each other as the first projection enters the corresponding slot. The first and second alignment features align the first and second parts of the clip in a thickness direction parallel to sutures passing through the suture engagement region, such that the first part is prevented from moving relative to the second part in the thickness direction when the first and second parts are attached together.

In some embodiments, the first engagement features are offset from the second engagement features, in the thickness direction, in a width direction extending between the first and second projections, or in both the thickness and width directions. The engagement first features can comprise first ledges and the second engagement features comprise second ledges, and the first ledges can be offset from the second ledges in the thickness direction such that the first ledges and the second ledges overlap each other to form a tortuous suture pathway through the suture engagement region. In some embodiments, the suture engagement region is configured to cut off free ends of sutures.

In some embodiments, the first part and the second part each include holes or other features for securing the first and second parts to a larger prosthetic device, such as a prosthetic heart valve or annuloplasty ring, such that the suture clip can be used to secure the larger prosthetic device to sutures extending from the native tissue.

In some embodiments, the first part and the second part of the suture clip include recesses located on opposing sides of the suture clip for engagement with a suture clip gripping device, wherein compression applied by the gripping device to the recesses causes the projections to move into the corresponding slots.

In some embodiments, the first and second parts lock together via a ratcheting locking engagement between the projections and the corresponding slots, such that the suture clip can be locked together at different positions.

An exemplary multi-clip delivery device comprises a handle having a trigger and an elongated shaft portion configured to hold a plurality of suture clips. The device is configured to attach each of the held suture clips one-at-a-time to sutures by compressing two opposing parts of the suture clip together and causing the two opposing parts of the suture clip to lock together and clamp onto one or more sutures passing between the two parts of the suture clip. The delivery device can include two compression members that are configured to apply compression on the two parts of a suture clip upon actuation of the trigger in order to deploy the distal-most one of the suture clips, and after deployment of a suture clip, the delivery device is configured to advance the remaining suture clips held in the shaft portion such that a next most distal suture clip can be deployed by actuating the trigger again.

In some embodiments, for each suture clip held by the delivery device, the two parts of the suture clip are held in an un-engaged configuration, and compression applied by the compression members causes the two parts of the suture clip to engage with each other and become locked together around one or more sutures. In some embodiments, the two compression members are joined at a pivot joint within the shaft portion. In some embodiments, the two compression members comprise jaws at their distal ends that fit within recesses in the two parts of a suture clip being deployed. Some embodiments comprise rods within the shaft portion that are configured to advance the remaining held suture clips after each suture clip has been deployed.

The foregoing and other objects, features, and advantages of this disclosure will become more apparent from the following detailed description, which proceeds with reference to the accompanying figures.

BRIEF DESCRIPTION OF THE DRAWINGS

FIG. 7 shows the left and right parts of the clip of FIG. 5 further joined together. FIG. 8 also shows the left and right parts of the clip of FIG. 5 further joined together.

FIG. 9 is a cross-sectional view of the clip in the configuration of FIG. 7 showing a suture passageway through the clip. FIG. 10 is another cross-sectional view of the clip in the configuration of FIG. 7 showing a suture passageway through the clip.

FIG. 20A illustrates another exemplary device for delivery and clamping two parts of a suture clip together. FIG. 20B further illustrates a distal end portion of the device of FIG. 20A.

FIG. 21A shows an exemplary device for delivering two-piece suture clips. FIG. 21B further illustrates a distal end portion of the device of FIG. 21A.

FIG. 22A shows another exemplary device for delivering two-piece suture clips. FIG. 22B further illustrates a distal end portion of the device of FIG. 22A.

DETAILED DESCRIPTION

Described herein are systems and methods for securing sutures that obviate the need for tying knots. Instead of tying two ends of a suture or two or more sutures together with a knot, the suture portions can be secured using the disclosed clips and/or other securement devices. A suture securement device can be applied to a single suture portion, or to two or more adjacent suture portions, that extend from tissue and/or from implanted objects. Disclosed suture clips and other devices can be used anywhere in a patient's body, including at or adjacent the heart, blood vessels, or other organs.

While this disclosure primarily describes securing individual suture portions or securing two suture portions together, embodiments of the disclosed devices, systems, and methods can also be used to secure three or more suture portions together in a similar matter. The suture portions being secured together can be two portions of the same suture (e.g., opposite ends) or portions of different sutures. Furthermore, the suture portions secured together can be any portion along a length of a suture, such as an end of the suture or a portion of the suture between its ends.

The disclosed devices, systems, and methods can be used with various types of sutures, threads, cords, wires, cables, lines, filaments, or similar objects (which are collectively referred to herein as "sutures" for ease of description). Exemplary suture materials can include biological tissues (e.g., collagen-based tissue), polyglycolide, polydioxanone, polyester, nylon, polypropylene, and other polymeric materials. Some sutures comprise several strands of fibers braided or woven together.

The disclosed suture clips can generally be used individually or as part of another device, unless specifically described otherwise. For example, any of the clips disclosed herein can be applied to sutures as a free-floating clip that secures one or more sutures adjacent a location where the suture(s) exit tissue or another implanted device. In embodiments wherein the clip is placed against or adjacent to tissue, pledget material can be bonded or coupled to the tissue facing side of the clip parts in order to protect the tissue, improve healing of the tissue, and/or reduce leakage.

In other embodiments, the disclosed suture clips can be incorporated into a larger prosthetic device, such as a prosthetic heart valve or annuloplasty ring, optionally along with a plurality of other similar suture clips, in order to secure the prosthetic device in the body via sutures grasped by the clips.

The terms "left" and "right" are used herein merely as a convenient way to describe parts of suture clips, though these terms do not limit the referenced parts as requiring usage or placement on a left or right side of anything.

Figure 1:
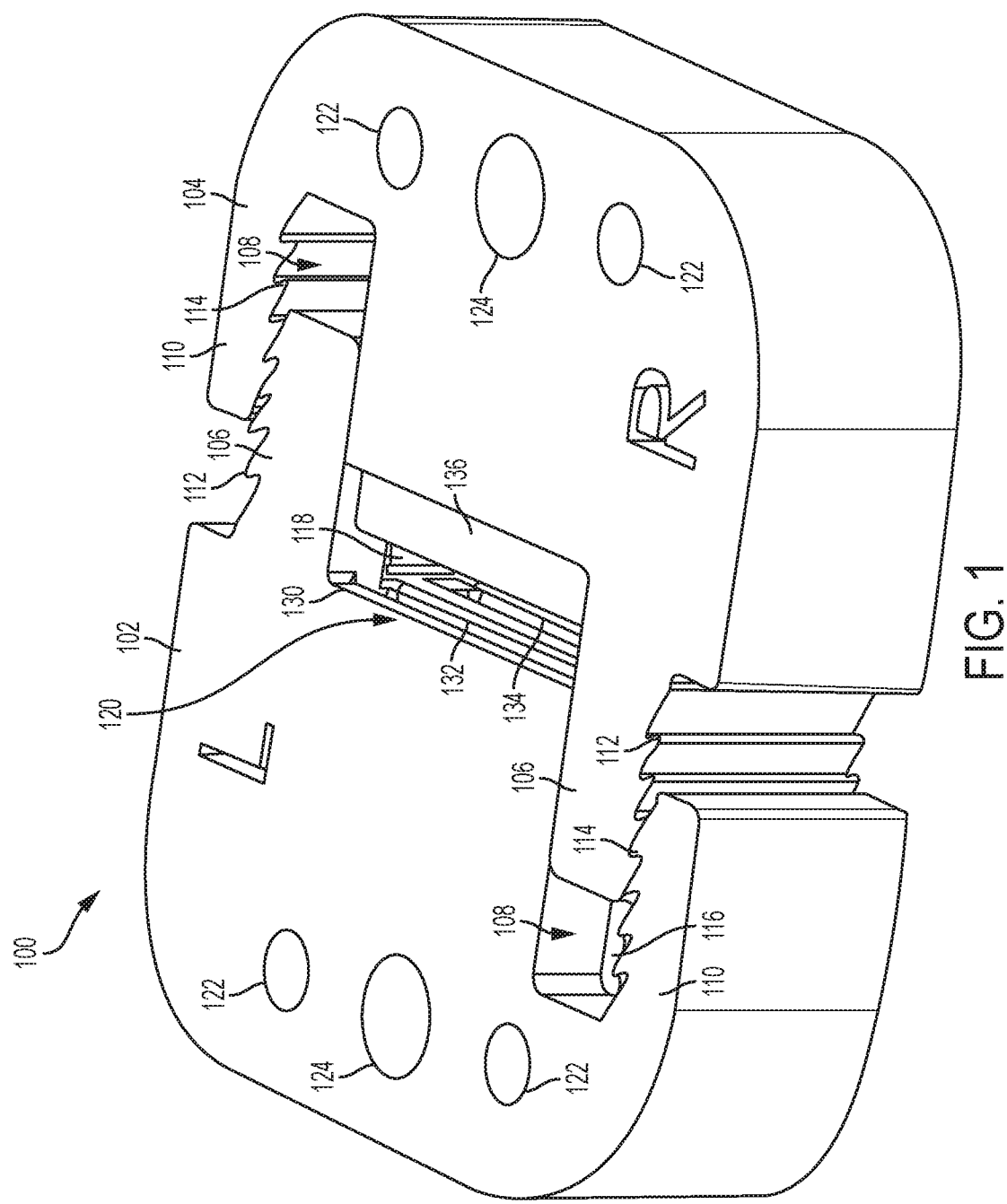
FIG. 1 is a perspective view of an exemplary suture clip comprising two parts that clip together to capture a suture between them.

FIG. 1 shows an exemplary suture clip 100 that comprises a left part 102 and a right part 104 that are brought together to secure the clip onto one or more sutures passing through a suture engagement region 120. In this embodiment, the left and right parts 102, 104 can include the same or similar features, and thus the clip 100 can have some degree of symmetry. The upper side of the clip 100 (e.g., the surfaces with the "L" and "R" in FIG. 1) can face away from tissue or other object from which the secured sutures extend, while the bottom side of the clip (e.g., opposite from the upper side) can contact the tissue or other object from which the suture extend. Thus, after the clip 100 is secured onto one or more sutures, a tensioned portion of the secured sutures can extend from the bottom side of the suture engagement region 120 and loose or free ends of the sutures can extend from the upper side suture engagement region.

As shown at the top of FIG. 1, the left part 102 can include a projection 106 that is inserted into a slot 108 in the right part 104. The slot 108 can be partially formed by an arm 110 of the right part 104. As the projection 106 enters the slot 108, teeth 112 on the projection 106 interengage with teeth 114 on the arm 110. The angled shape of the teeth 112, 114 create a ratcheting effect that allows the projection 106 to enter the slot 108 but prevents the projection from moving out of the slot. A similar ratcheting locking mechanism is shown at the bottom of FIG. 1 on the opposite side of the suture engagement region 120, but comprising a projection 106 of the right part 104 that enters a slot 108 of the left part 102. Due to the plurality of closely spaced teeth 114, 112, the suture clip can be locked together at different positions corresponding to each different combination of the teeth 112 with the teeth 114. For example, in FIG. 1, the clip 100 is locked at one possible position, but the first and second parts can be clamped together to three alternative positions that are closer/tighter that the position shown by moving the projection further into the slots. At each successively tighter position, each tooth 112 on the projections 106 engages with a different tooth 114 deeper into the slots 108. These different alternative locked positions correspond to different sizes of the suture pathway through the suture engagement region 120, which allow for clamping onto different sized sutures, for example. This can allow the left and right parts 102, 104 to be locked together during delivery and/or while sutures are threaded through the suture engagement opening 120, then clamped to a tighter locked position to secure the sutures.

In some embodiments, the locking mechanism may be releasable such that the clip parts can be unlocked, separated, and/or re-deployed. In such embodiments, the clip can be closed onto a suture without cutting the suture. If the placement on the suture is undesirable, the clip can be unlocked and opened and removed from the suture, and optionally re-deployed in a more desirable position or disposed of. Manual cutting of the sutures may be performed when using such suture clips.

In the embodiment shown in FIG. 1, and in other illustrated embodiments, the two locking mechanisms to secure the left and right parts of the clip together are generally symmetrical, though in other embodiments variations of the illustrated configurations can be used. For example, in some embodiments, both of the male portions (e.g., projections 106) can be included in one of the clip parts (e.g., the left part 102) and both of the female portions (e.g., slots 108) can be included in the other clip part (e.g., the right part 104). In some embodiments, only one of the interfaces between a projection 106 and a slot 108 can include a locking mechanism, such as the teeth 112, 114, while the other projection/slot interface can be smooth to provide a guided inter-engagement without a locking mechanism. In other embodiments, the other types of locking mechanisms can be included to secure the left and right parts together.

In other embodiments, the suture clip can include only one projection included in one of the two parts and corresponding slot included in the other part. In such embodiments, the projection and slot can be located at one end of the suture engagement region and can include a locking mechanism. At the opposite end of the suture engagement region, the two clip parts can have any suitable interface.

Figure 5:
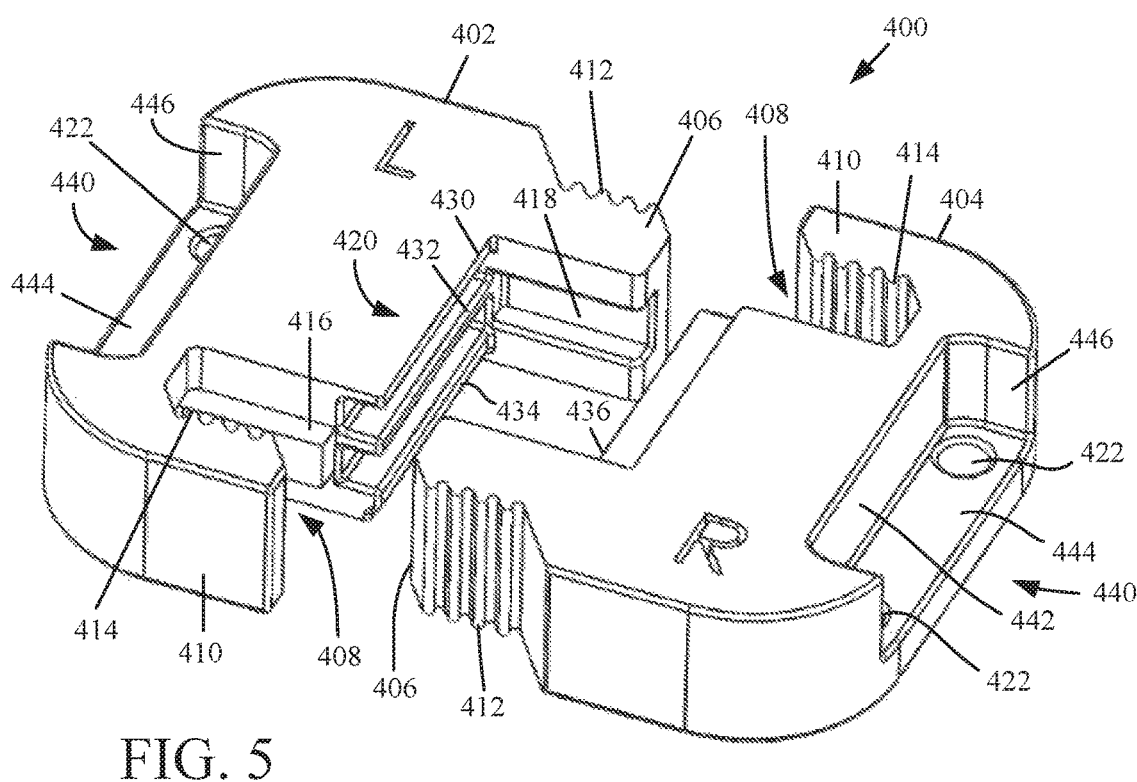
FIG. 5 shows left and right parts of another exemplary suture clip.
Figure 6:
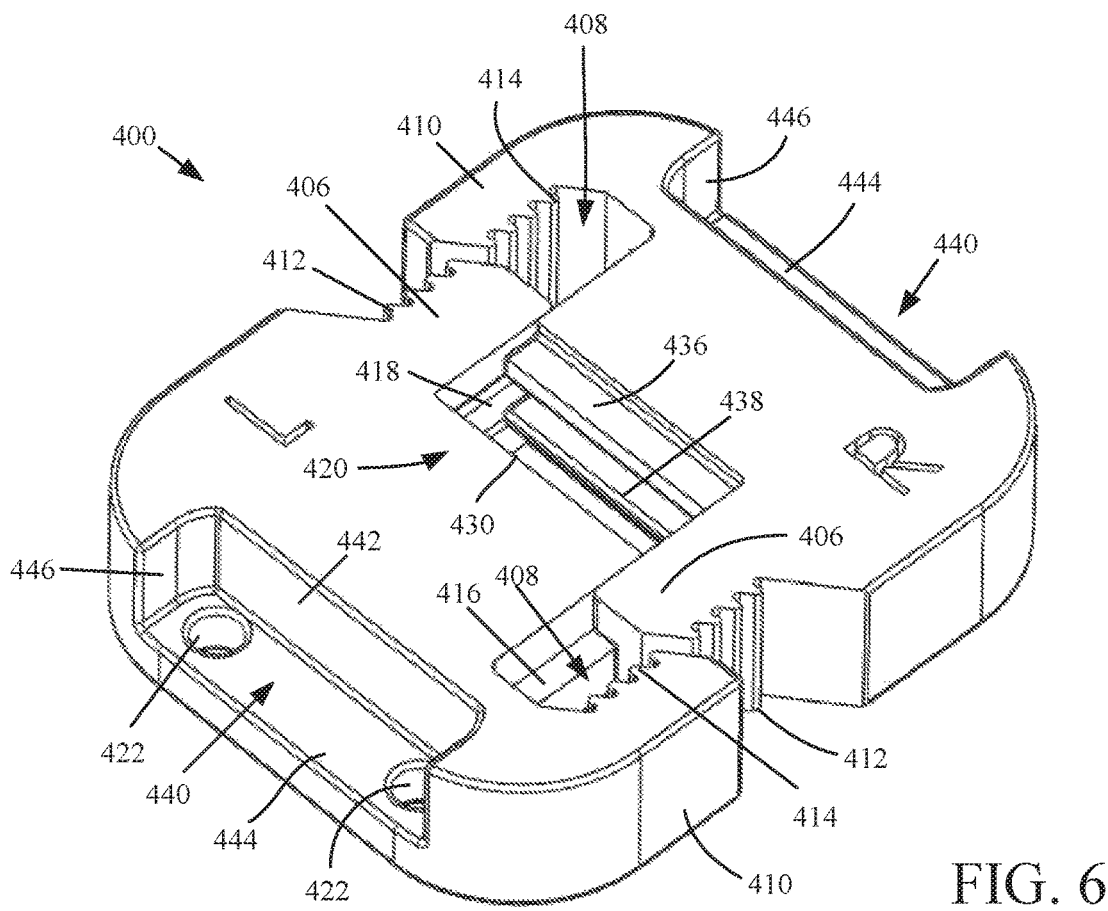
FIG. 6 shows the left and right parts of the clip of FIG. 5 partially joined together.
Figure 11:
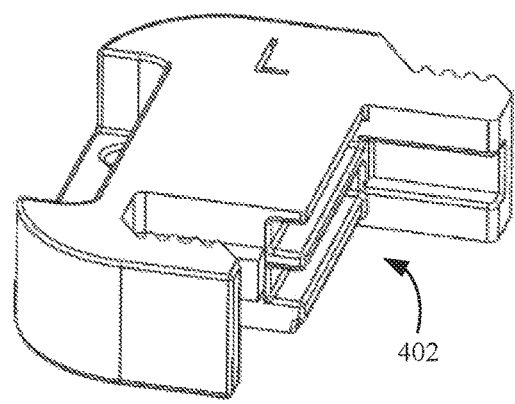
FIG. 11 is a perspective view of the left part of the clip of FIG. 5.
Figure 12:
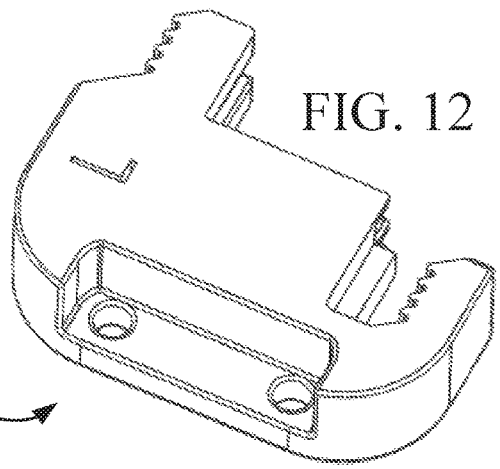
FIG. 12 is another perspective view of the left part of the clip of FIG. 5.
Figure 13:
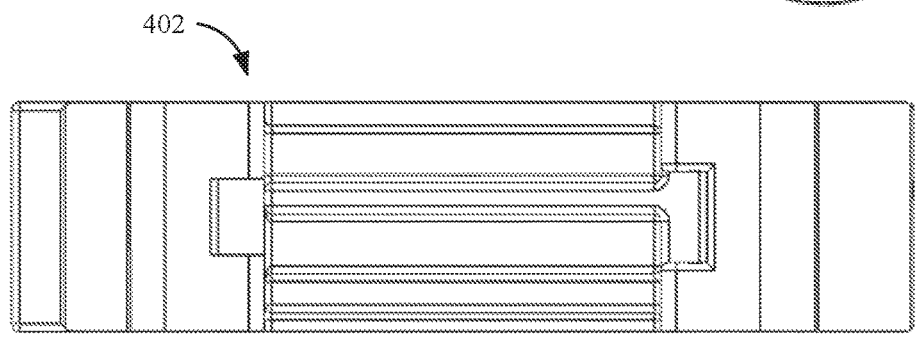
FIG. 13 is an orthogonal side view of the left part of the clip of FIG. 5.
Figure 14:
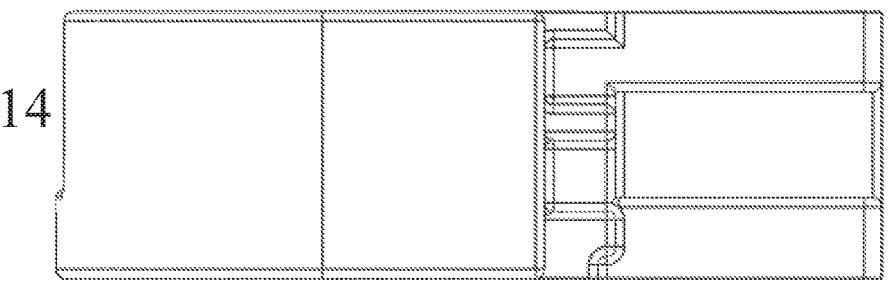
FIG. 14 is another orthogonal side view of the left part of the clip of FIG. 5.
Figure 15:
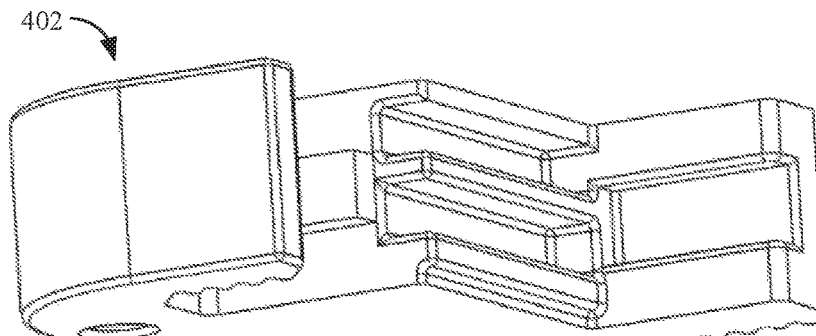
FIG. 15 is yet another perspective view of the left part of the clip of FIG. 5.
Figure 16:
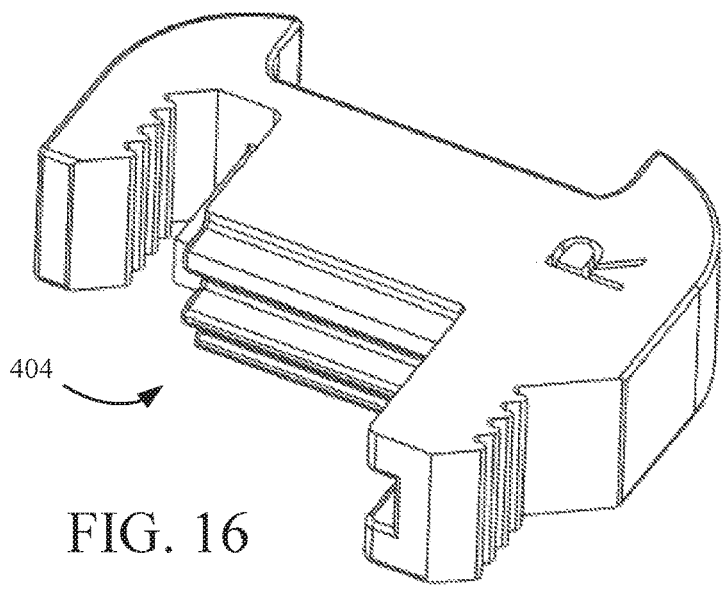
FIG. 16 is a perspective view of the right part of the clip of FIG. 5.
Figure 17:
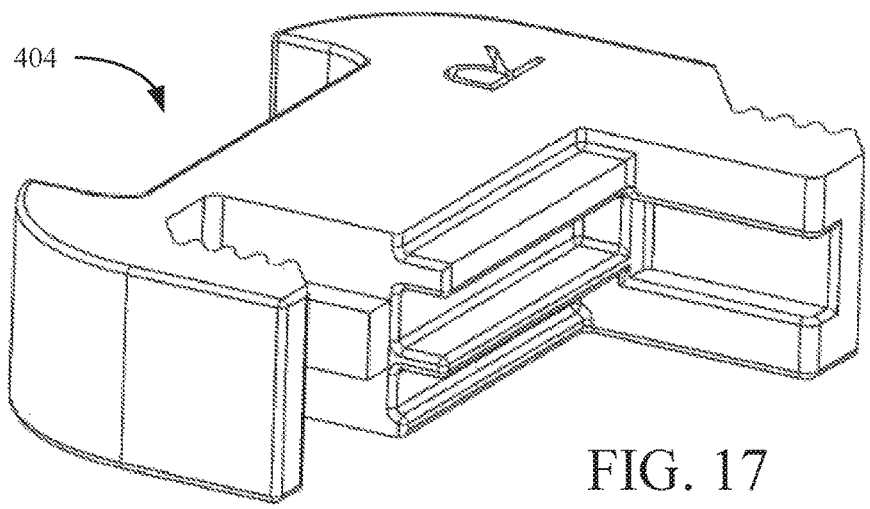
FIG. 17 is another perspective view of the right part of the clip of FIG. 5.
Figure 18:
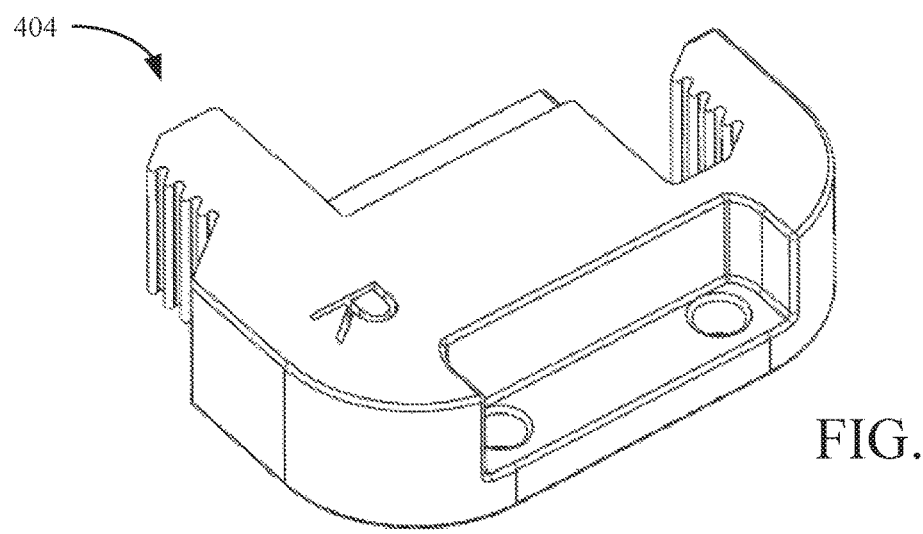
FIG. 18 is yet another perspective view of the right part of the clip of FIG. 5.

As the left and right parts 102, 104 are brought together, their mutual alignment can be controlled in part by one or more horizontal ridges 116 (see bottom of FIG. 1) located along the inner sides of the slots 108 that mate with corresponding horizontal grooves 118 (see top of FIG. 1) located on the inner sides of the projections 106. (Similar horizontal ridges 416 and grooves 418 are more clearly illustrated in FIGS. 5 and 6 with respect to the suture clip 400.) The interface between the ridges 116 and grooves 118 can help guide the projections 106 into the slots 108 while preventing relative motion between the two parts 102, 104 in the direction of the thickness of the clip (e.g., the direction between the upper side and the lower side of the clip).

Figure 2:
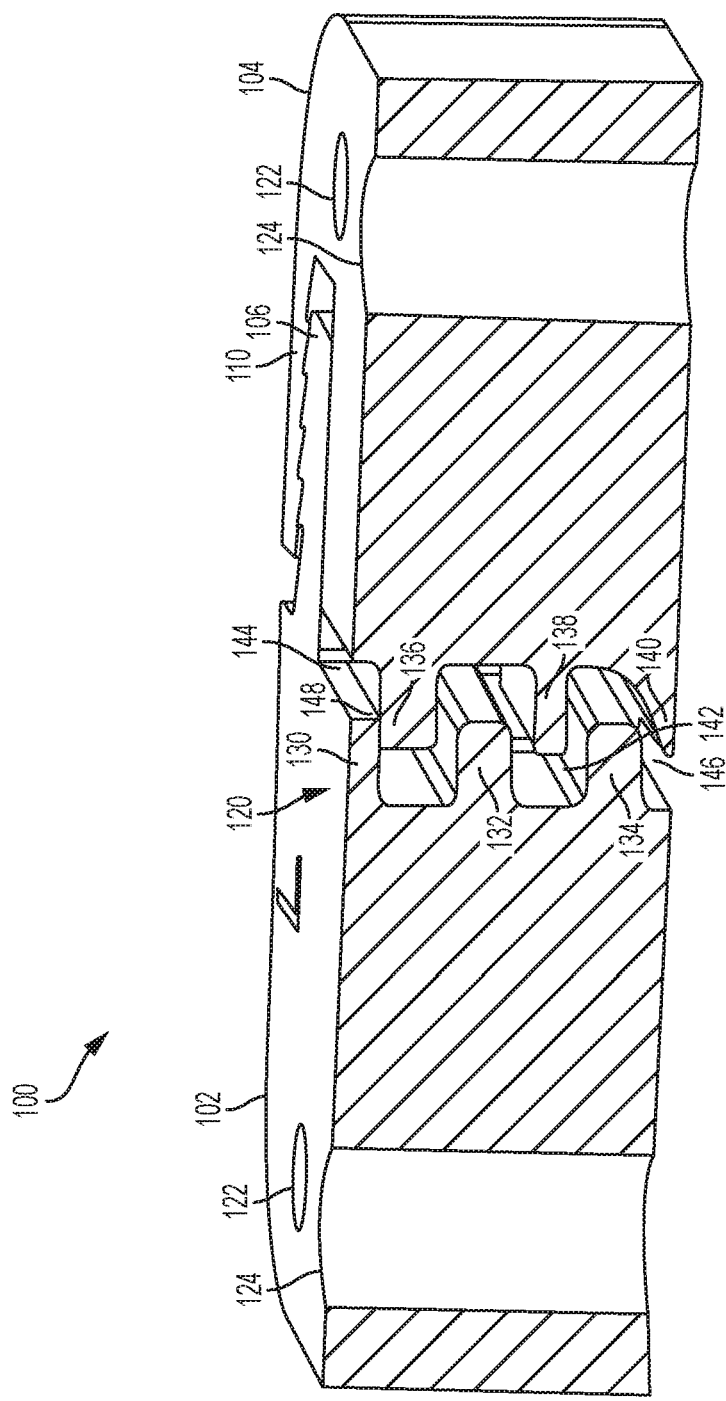
FIG. 2 is a cross-sectional of the suture clip of FIG. 1, showing a suture passageway through the clip.

As further shown in FIG. 2, the suture engagement region 120 can include a tortuous passageway 142 that winds between ledges 130, 132, 134 of the left part 102 and ledges 136, 138, 140 of the right part 104. In other embodiments, fewer or more ledges can be provided on either or both of the left and right parts. The ledges of the left part 102 can be offset in the thickness direction relative to the ledges of the right part 104 to create the tortuous passageway 142. When one or more sutures are present in the passageway 142 (such as after a surgeon has applied a desired tension to the sutures), the sutures can become compressed between the offset inter-engaging ledges as the left and right parts are compressed together, thereby retaining the sutures within the clip 100 at a desired tension and preventing slippage of the sutures through the passageway 142. When the clip 100 is clamped together as shown in FIG. 2, the inter-engagement of the ledges can also help prevent separation of the left and right parts of the clip in the thickness direction.

When the left and right parts 102, 104 are compressed together, a sharp interface between the uppermost ledges 130 and 136 (or other pairs of ledges) can cut the sutures, such that free ends of the sutures can be removed from the upper end 144 of the passageway while tensioned portions of the sutures remain extending from the lower end 146 of the passageway into the adjacent tissue or other object. The gaps between adjacent ledges can be sized based on the thickness and type of sutures such that a desired degree of compression and friction is applied to the sutures to retain them. The presence of the projections 106 on either end of the suture engagement region 120 (see FIG. 1) blocks engaged sutures from sliding laterally out of the clip.

In some embodiments, some or all of the ledges 130, 132, 134, 136, 138, 140 can include sand-blasted surfaces to make those surfaces rougher and create more friction to improve suture retention. The surfaces that engage to shear the sutures may not be sand-blasted to provide a sharp interface.

As shown in FIG. 1, the left and right parts 102, 104 can include holes 122 and 124 that can be used for various purposes, such as grasping the parts and clamping the parts together. The holes 122 and/or 124 can also be used for securing the clip 100 to another object, such as to a prosthetic heart valve, ring, pledget, or other implanted device. In some embodiments, a delivery device can include projections that insert into the holes 122 and/or 124 in order to hold the parts 102, 104, move the parts 102, 104 over sutures, and clamp the parts 102, 104 together. In some embodiments, sutures or other objects can pass through the holes 122 and/or 124 to secure the left and right parts of the clip 100 to another implanted object. In some embodiments, a needle driver or plier-like device can be used to hold and clamp the clip 100 by inserting clamping ends of the device into the holes 124 and actuating a handle portion the device to clamp the clip.

Figure 3:
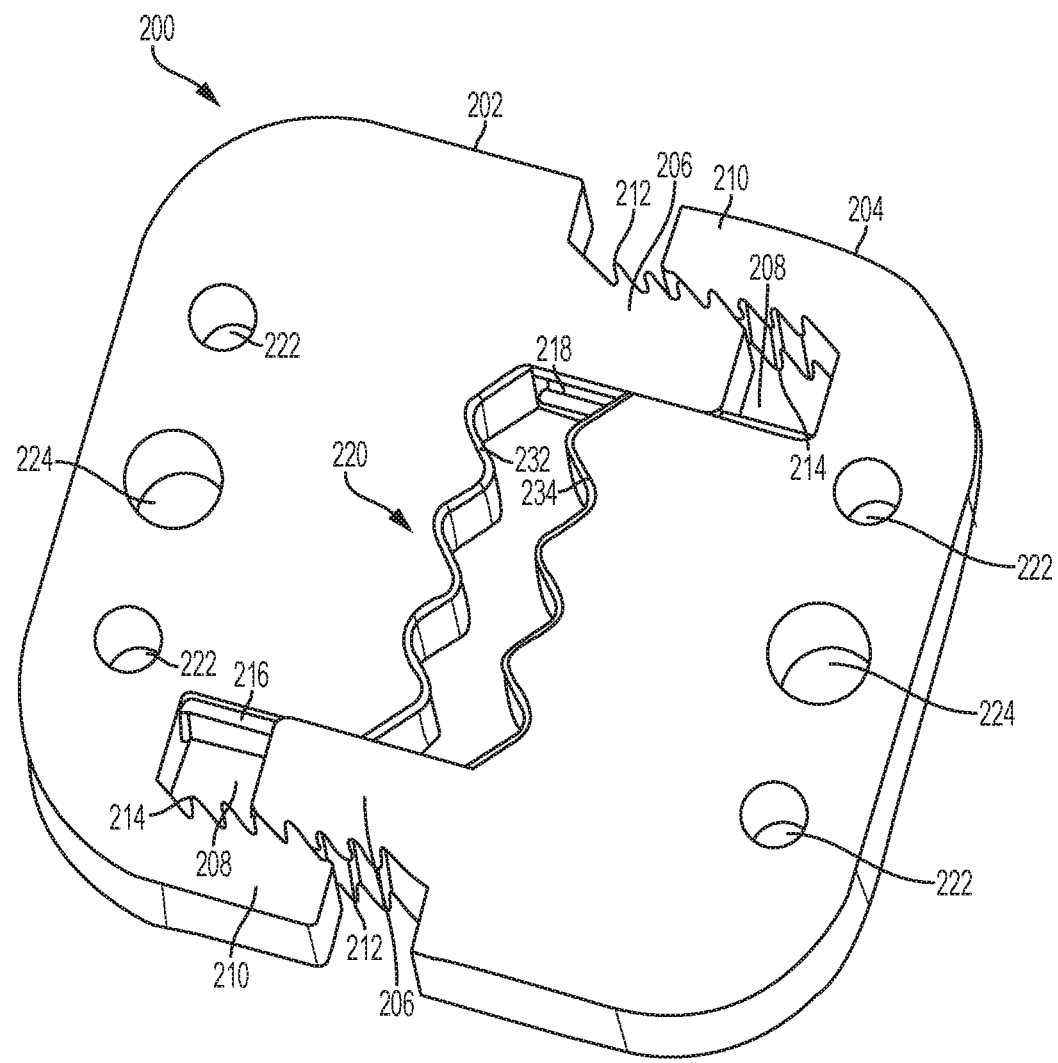
FIG. 3 is a perspective view of an alternative suture clip comprising two parts that clip together to capture a suture between them.

FIG. 3 shows another exemplary suture clip 200 that is similar to the clip 100 but with a differently configured suture engagement region Like the clip 100, the clip 200 includes a left part 202 and a right part 204, each having a projection 206, a slot 208, arm 210, inter-engaging teeth 212, 214, ridges 216 and grooves 218, and holes 222 and 224. The suture engagement region 220 comprises an undulating surface 232 on the left part 202 and a corresponding undulating surface 234 on the right part. When the left and right parts are brought together, the undulating surfaces 232 and 234 mate together to clamp one or more sutures passing therebetween. The undulating surfaces can help restrict the sutures from moving laterally toward the projections 206 at either end of the suture engagement region 220.

Figure 4:
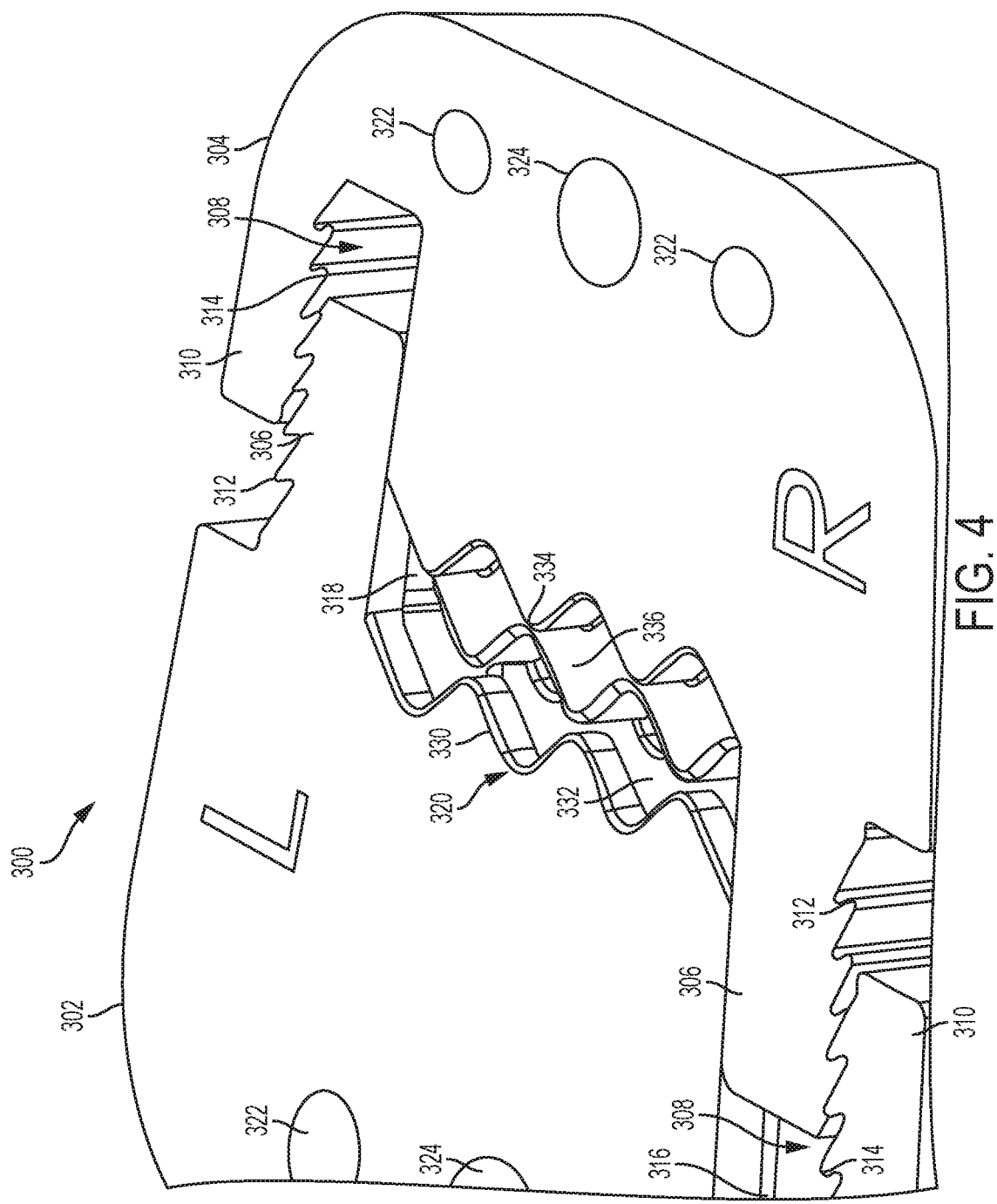
FIG. 4 is a perspective view of another alternative suture clip comprising two parts that clip together to capture a suture between them.

FIG. 4 shows another exemplary suture clip 300 that is similar to the clips 100 and 200 but with a differently configured suture engagement region Like the clips 100 and 200, the clip 300 includes a left part 302 and a right part 304, each having a projection 306, a slot 308, arm 310, inter-engaging teeth 312, 314, ridges 316 and grooves 318, and holes 322 and 324. The suture engagement region 320 comprises an undulating surface a combination of the offset ledges of the clip 100 and the undulating surfaces of the clip 200. As shown in FIG. 4, left part 302 includes an uppermost undulating ledge 330 and at least one lower undulating ledge 332, while the right part 304 includes an uppermost undulating surface 334 and at least one undulating ledge 336. As the left and right parts 302, 304 are brought together, the uppermost undulating ledge 330 of the left part 302 mates with the corresponding undulating surface 334 of the right part 304, and the undulating ledge 336 of the right part moves between the undulating ledges 330, 332 of the left part and mates with a corresponding recessed undulating surface of the left part (not visible in FIG. 4) positioned between the ledges 330 and 332. Additional lower undulating ledges can also engage together in a similar way. In some such embodiments, two of the ledges can shear off the free ends of the sutures as the ledges overlap each other, with as the top ledges 330 and 336. Other lower ledges can be spaced from each other in the thickness direction to provide space for the sutures the snake down through the suture engagement region 320, like in the clip 100.

FIGS. 5-18 illustrate another exemplary suture clip 400 that is similar to the clip 100 with recessed gripping portions on the lateral sides of the two parts. Like the clip 100, the clip 400 includes a left part 402 and a right part 404, each having a projection 406, a slot 408, arm 410, inter-engaging teeth 412, 414, ridges 416 and grooves 418, and holes 422. The suture engagement region 420 is similar to the suture engagement region 120 of the clip 100 and includes ledges 430, 432, 434 on the left part 402 and offset ledges 436, 438, 439 on the right part 404. A tortuous suture passageway is formed between the offset ledges with a lower end 450, an upper end 452, and a suture shearing interface 454 formed between the uppermost ledge 430 and the opposing ledge 436 below.

The left and right parts 402, 404 also include recesses 440 for engagement with a gripping device, such as the gripping devices shown in FIGS. 19-22. Each recess 440 can partially be defined by a lower surface 440, an inner surface 442, and side surfaces 446. Holes 422 can pass through the lower surfaces 440 and can be used to attach the left and right parts to another device. Using the gripping device 500 as an example (FIGS. 19A and 19B), jaws 512 and 514 of the device 500 can be placed in the recesses 440 and clamped toward each other to secure the left and right parts 402, 404 together. The jaws 512, 514 can presses against the inner surfaces 442 to apply the clamping force. The lower surfaces 442 and side surfaces 446 can help align the jaws in the recesses 440.

In some embodiments, the left and right parts 402, 404 can be pre-attached to another larger prosthetic device (e.g., via holes 422) before a gripping/pinching device is applied. Optionally, the projections 406 can also be pre-inserted partially into the slots 408 before the gripping device is applied to ensure proper alignment. A surgeon can thread the sutures through the suture engagement regions 420 of how many ever suture clips 400 are included with the larger prosthetic device, parachute the larger prosthetic device down over the sutures to the desired placement against the native tissue, apply a desired degree of tension to the sutures, and then use a gripping device to clamp the left and right parts 402, 404 together to secure the sutures at the desired tension. Each individual suture clip 400 can be clamped in succession with a gripping device such as those shown in FIGS. 19-22. Various other types of gripping devices can alternatively be used instead of the devices illustrated.

In some embodiments, the suture clip 400 can be free-floating and not pre-attached to a larger prosthetic device. In such embodiments, the suture clip 400 can be held and delivered into the body and over sutures using a device that is capable of both holding onto the clip and clamping the clip. For example, the jaws 512, 514 of the device 500 in FIGS. 19A and 19B can fit tightly into the recesses 440 such that friction keeps the left part 402 suspended on the jaw 512 and the right part 404 on the jaw 514. The left and right parts 402, 404 may also be partially pre-engaged with each other with the projections 406 partially inserted into the slots 408. In such embodiments, a gentle compression between the jaws 512, 514 against the inner surfaces 442 can be sufficient to hold the clip 400 in the device 500 as the clip in inserted into the both and threaded over sutures. The clip 400 can be threaded over the suture(s) toward the point where the suture(s) exit the native tissue or where the suture(s) exit another larger prosthetic device that has previously been placed over the suture(s). For example, a prosthetic heart valve can be parachuted over several pre-placed sutures extending from the native valve annulus, with the sutures passing through an outer ring of the prosthetic heart valve, and then the clips 400 can be guided with the device 500 over the sutures (such as one clip for each pair of two sutures) down against the surface of the outer ring. The sutures can then be tensioned and the device 500 can be actuated to clamp the clips 400 onto the tensioned sutures. Excess suture material can be shorn off during the clamping process via the shearing interface 454 (FIG. 9).

Figures 19A, 19B:
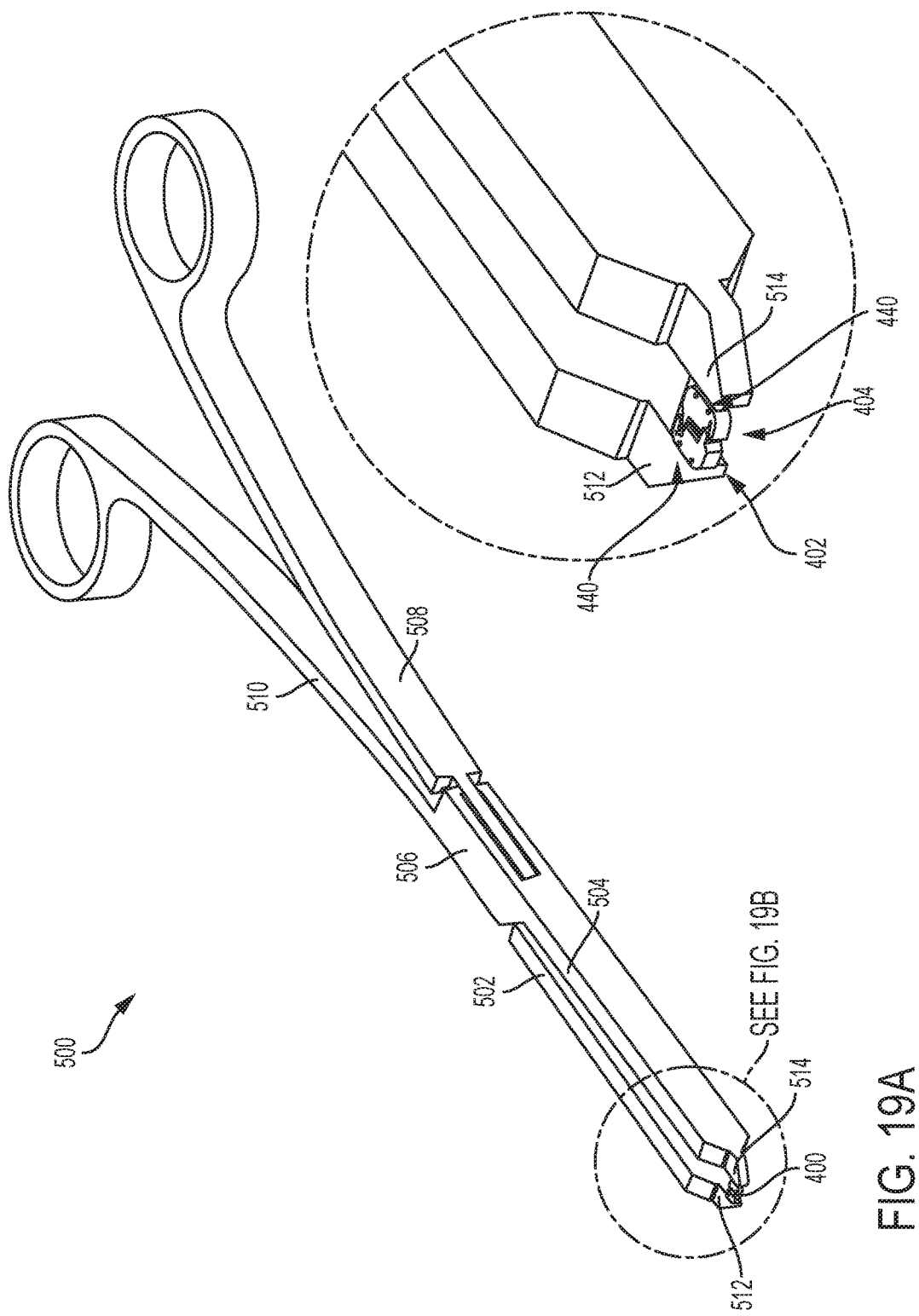
FIG. 19A illustrates an exemplary device for delivery and clamping two parts of a suture clip together.
FIG. 19B further illustrates a distal end portion of the device of FIG. 19A.

As shown in FIGS. 19A and 19B, the gripping device 500 can comprises a first member 502 with a first jaw 512 and a first arm 508, and a second member 504 with a second jaw 514 and a second arm 510. The two members 502, 503 are pivotably coupled at a joint 506 such that moving the arms 508, 510 toward each other moves the jaws 512, 514 toward each other to clamp a clip such as clip 400 as illustrated. As shown in FIG. 19B, the jaws 512, 514 can include inward projections that engage with recesses 440 in the outer sides of the clips parts 402, 404.

FIGS. 20A and 20B show an exemplary suture clip gripping device 600 that is similar to the device 500, but it holds the clip pieces in an orientation rotated 90 degrees from the device 500. The gripping device 600 comprises a first member 602 with a first jaw 612 and a first arm 608, and a second member 604 with a second jaw 614 and a second arm 610. The two members 602, 604 are pivotably coupled at a joint 606 such that moving the arms 608, 610 toward each other moves the jaws 612, 614 toward each other to clamp a clip, such as clip 400 as illustrated. As shown in FIG. 20B, the jaws 612, 614 can include inward projections that engage with recesses 440 in the outer sides of the clips parts 402, 404.

In an alternative gripping device, the device similarly includes two arms that pivot at a joint and the ends of the arms include inwardly projecting flanges that are configured to register with inwardly recessed notches in the left and right parts of a suture clip. The notches can be located just above outwardly projecting shelves that also help align the ends of the arms with the left and right parts. Such a registered engagement can prevent the left and right parts of the clip from disengaging from the gripping device until the arms are spread apart to release the clip after sutures have been secured within the clip.

FIGS. 21A, 21B, 22A, and 22B show exemplary suture clip delivery devices 700 and 800 that can hold a single suture clip or a plurality of suture clips (e.g., 10-20 clips in some embodiments) and can deliver the held clips in succession onto sutures within the body without having to reload the device. Using the example of a prosthetic heart valve being implanted at a native valve annulus in the heart, a surgeon can first place sutures in the native tissue, thread the sutures through an outer ring (e.g., a sewing ring or a rigid ring with apertures) of the prosthetic heart valve, and parachute the prosthetic heart valve over the sutures against the native tissue. The clip delivery device 700 or 800, preloaded with sufficient suture clips, can be used to clamp suture slips onto the sutures. In some embodiments, the sutures can be fed into a distal end of the device, pulled to a desired tension, and then the device can be actuated to clamp a suture clip onto the tensioned sutures. When the device is preloaded with a plurality of suture clips, the device can be used to quickly place several suture clips around the prosthetic heart valve to secure it at several points without have to retract the device out of the body and reload it with more clips.

As shown in FIGS. 21A and 21B, the device 700 includes a handle 702 with a trigger 704, and an elongated shaft portion 706 that houses the suture clips 710 (which can be similar to any of the clips 100, 200, 300, or 400). FIG. 21B shows an enlarged view of the distal portion 708 of the device 700 that includes elongated rod-like members 712 that engage the suture clips 710 by extending longitudinally through openings in each piece of the suture clip.

FIGS. 22A and 22B show a delivery device 800 that includes a handle 802 with a trigger 804, and an elongated shaft portion 806 that houses a plurality of suture clips 810 (which can be similar to any of the clips 100, 200, 300, or 400). FIG. 22B shows an enlarged view of the distal portion 808 of the device 800 that includes elongated rod-like members 812 that engage the suture clips 810 by extending longitudinally through openings in each part of the suture clip. One set (e.g., two) of rods 812 extend through all the left-hand clip parts, and another set (e.g., two) of rods 812 extends through all the right-hand clip parts. One or more pushing members (not shown) within the shaft portion 806 can push the clips 810 distally within the shaft portion and/or within a discrete clip magazine positioned inside the distal portion 808 of the shaft portion 806 to advance the clips after each distal-most clip is deployed. Pushing members can be spring actuated, or otherwise configured, to bias the clips distally.

A gripping portion 814 can be included within the distal portion 808, such that the gripping portion 814 can grip the distal-most suture clip parts, allow the rods 812 to retract out of them, and then clamp the distal-most suture clip onto sutures extending through a central opening 822, which passes between the left and right clip parts. The gripping portion 814 can then release the clamped clip, allow the remaining clips to be advanced distally, and then grip the next most-distal clip to repeat the process. The gripping portion 814 can include two arms 830, 832 that pivot at joint 834 to cause jaws 836, 838 to actuate. The jaws 836, 838 can include inward projections that engage with recesses (e.g., recesses 440 in clips 400) in the outer sides of the clip parts.

The sutures, after being inserted through central opening 822, can be gripped proximal to the clips 810 by a tensioning device (not shown) that applies a desired tension to the sutures prior to clamping the clip.

Pulling the trigger 804 of the device 800 can cause the jaws 836, 838 to clamp a distal-most clip 810 onto the tensioned sutures. Releasing the trigger 804 then releases the jaws 836, 838 from the clamped clip 810 and causes the rods 812 and/or a proximal pusher to advance the remaining clips distally through the shaft portion 806 such that the next distal-most clip becomes gripped by the jaws and ready from deployment.

Before the deployment of each clip 810, the corresponding sutures are threaded through the opening 822 passing through the suture clips, or at least through the one suture clip being deployed. After the clip is clamped onto the corresponding sutures, the device 800 can be moved to another location, placed over other sutures, and the next suture clip can be clamped onto those sutures. The sutures can be manually threaded through the opening 822, such as with a needle, or in other embodiments, a suction device or other mechanism can be included in the device 800 that draws the sutures through the opening 822.

In some embodiments, the shaft portion 806 can include a lateral slot extending proximally from the distal end, wherein the lateral slot overlays a gap between the left and right parts of the clips 810 (e.g., the top and bottom in the example of FIG. 22B. In such embodiments, sutures can be moved laterally, radially into the suture engagement regions (e.g., the opening 822) through the slot in the shaft portion 806 and through the gap between the left and right parts of the clips 810. This can allow a user to tension the sutures and then apply the distal end of the shaft portion 806 laterally over the tensioned sutures such that the sutures move through the slot and into the suture engagement region of the clips. Then, when each clip is deployed, the free ends of the tensioned suture can be shorn off and removed, and the device 800 can be moved over to another location to apply the next clip to other sutures. This can obviate the need to retract the device 800 and thread each suture through the distal end of shaft portion and into the opening 822.

With any of the suture clip delivery devices and/or clamping devices disclosed herein, the device can include an elongated distal shaft that is malleable and/or made from malleable material, such that a user can bend the shaft to a desired shape and the shaft will remain in the bent shape while the device is used. For example, a the distal shaft can start out straight, and the user can impart one or more curves into the malleable shaft before inserting it into a patient's body. Such malleability can make it easier to access certain areas within the body with minimal intrusion and/or damage to other structures, and can also provide for a variety of different approach angles within the body that are not aligned with the proximal portion of the shaft.

In some embodiments, a delivery device similar to the device 800 can be used to deliver and deploy one or more suture clips via a transvascular approach. For example, percutaneous access can be made to provide access to the femoral artery and the delivery device can be inserted through femoral artery and the aorta into the heart. In such embodiments, the shaft portion of the delivery device can be flexible, steerable, and/or longer. The delivery device may also include additional features, such as an imaging device (e.g., a camera), a light source, proximally controllable actuators to control bending of the distal end of the device, a vacuum line for drawing sutures into the distal end of the device, etc. Such delivery devices may be used in conjunction with the implantation of transcatheter heart valves or similar devices that do not require surgical access into the heart.

In some embodiments, a device configured for clamping suture clips already present at the implantation site can be introduced into the heart through a transvascular approach, such as via a percutaneous access point and through the aorta. For example, a prosthetic heart valve that includes built-in suture clips can be threaded over sutures extending from the implantation site and parachuted over the sutures into contact with the tissue. Then to close the suture clips, a transvascularly delivered device can be used to apply a clamping force to the two parts of each suture clip to close the suture clip and lock the suture clip onto the sutures passing through the suture clip. The device can include an elongated, flexible, steerable shaft portion that extends through the vasculature, and handle portion with a trigger positioned outside the percutaneous access point, and actuating claws or compression members at the distal end that are configured to be placed over the two clip parts and exert a clamping force when the trigger is actuated. The device may also include additional features, such as an imaging device (e.g., a camera), a light source, proximally controllable actuators to control bending of the distal end of the device, etc. Such clamping devices may be used in conjunction with the implantation of transcatheter heart valves or similar devices that do not require surgical access into the heart.

Figure 23:
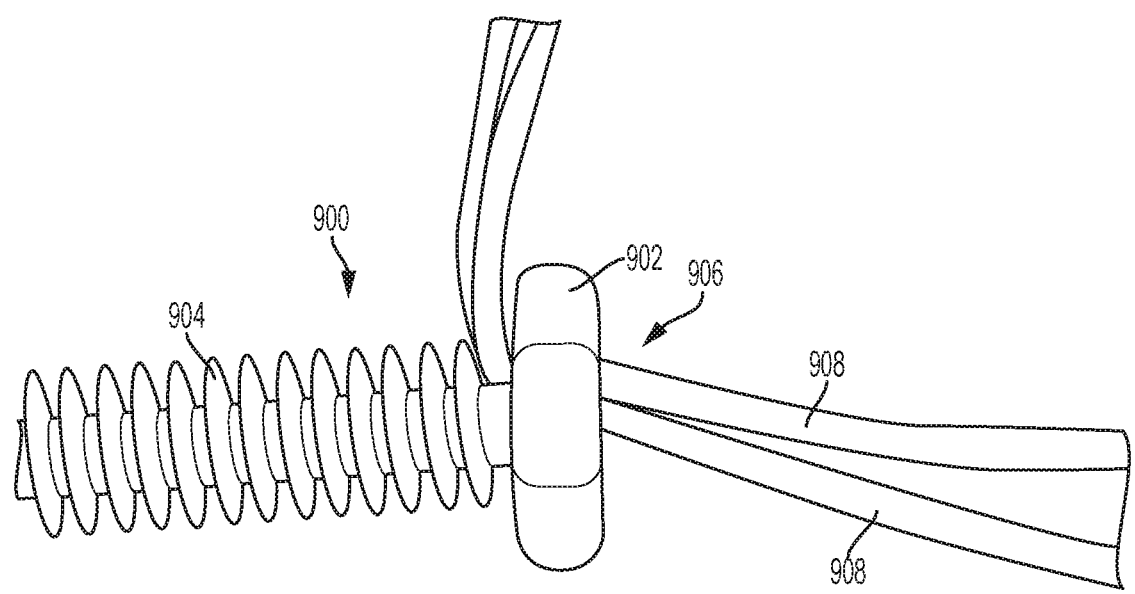
FIG. 23 shows an exemplary suture securement device having a threaded body and a head through which sutures extend.

FIG. 23 shows an alternative suture securement device 900 that comprises a nut 902 and a threaded screw 904. The nut 902 includes a threaded aperture 906 through which sutures 908 can be inserted. With the sutures 908 threaded through the nut 902, the screw 904 can be inserted into the nut and rotated to thread the screw through the nut, thereby securing the sutures between the outer threads of the screw and the inner threads of the nut.

Figure 24:
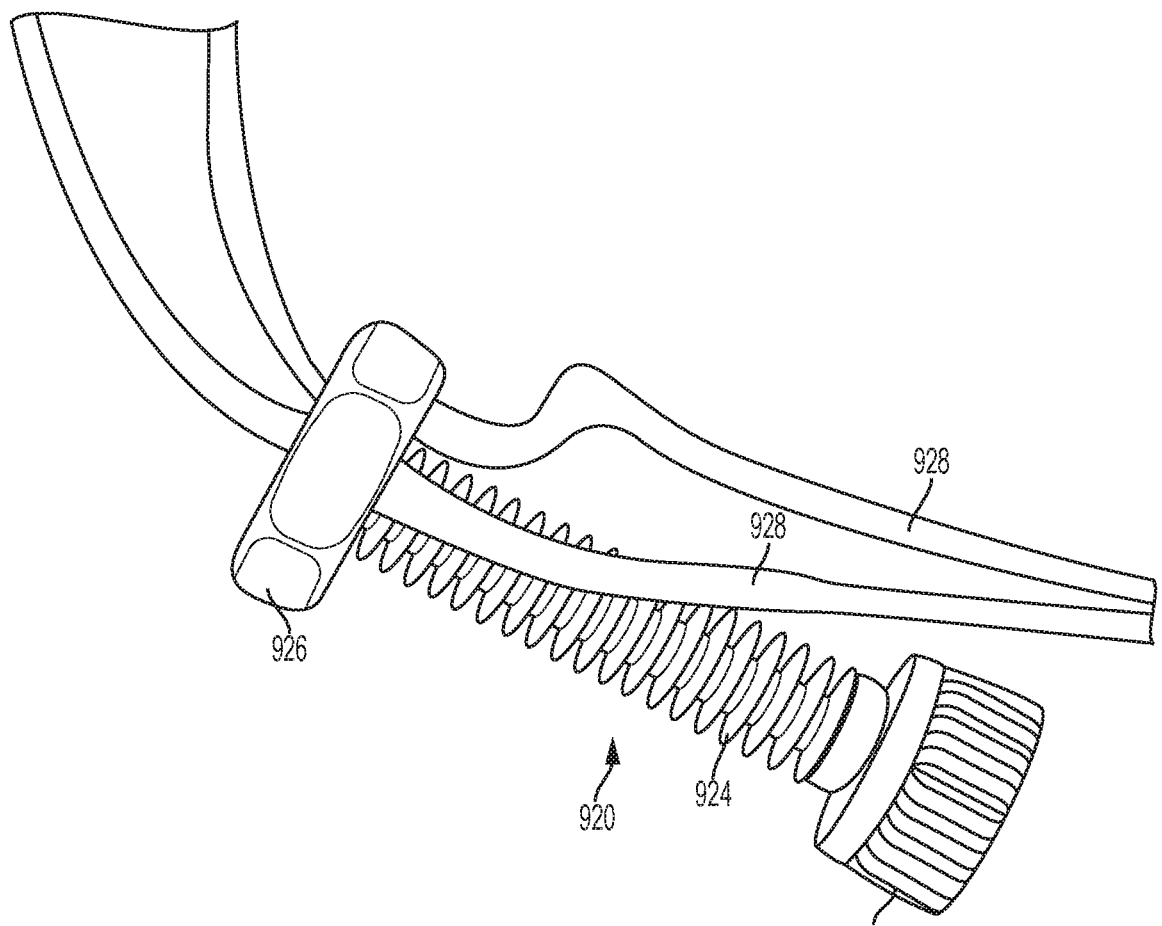
FIG. 24 shows another exemplary suture securement device having threaded screw and nut portions with a suture extending through the threaded interface.

FIG. 24 shows another exemplary suture securement device 920 that comprises a nut 926 and a threaded screw 924. The nut 926 includes a threaded aperture through which sutures 928 can be inserted. With the sutures 928 threaded through the nut 926, the screw 924 can be inserted into the nut and rotated by turning the head 922 to thread the screw through the nut, thereby securing the sutures between the outer threads of the screw and the inner threads of the nut.

For suture securement devices including a threaded engagement such as the devices 900 and 920, the nut or other portion having an internally threaded aperture can be part of, or attached to, a larger prosthetic device, such as a prosthetic heart valve. For example, an outer ring of a prosthetic heart valve can include a plurality of internally threaded openings and sutures pre-threaded through the native tissue can be inserted through the plurality of threaded openings. The externally threaded screw portion can then be inserted into the openings and screwed in to secure the sutures to the prosthetic heart valve. The screw portions can be delivered using a separate delivery device that can place each screw portion into one of the threaded openings and rotate the screw portion to drive it into the threaded opening. In other embodiments, the screw portions can be manually inserted and tightened by turning a head portion, like head 922 in FIG. 24.

In still other embodiments, the externally threaded screw portions can be part of, or attached to, a larger prosthetic device and the internally threaded nut portions can be placed over the sutures and then rotated (e.g., manually or with a delivery device) over the screw portions to secure the sutures to the prosthetic device. In embodiments using a delivery device, the delivery device can be configured to hold a plurality of nut portions or screw portions and configured to apply several of them in succession to secure sutures around the prosthetic device without having to reload the delivery device.

Some embodiments of devices disclosed herein can be used to secure sutures extending from opposite directions through the device, rather than sutures that extend in the same direction. For example, one or more sutures can extend from a first exit point in the tissue or a prosthetic device into the suture engagement region of a suture clip from one side, while one or more other suture ends extend from another exit point in the tissue or prosthetic device into the suture engagement region from the opposite side. In such an arrangement, the oppositely extending sutures can be secured together with the suture clip with their free ends projecting in opposite directions.

Any suitable materials can be used in the construction of the devices disclosed herein. For example, the suture clips and/or the clip delivery devices can comprise stainless steel, titanium, other metals or alloys, polymeric materials, and/or other suitable materials.

For purposes of this description, certain aspects, advantages, and novel features of the embodiments of this disclosure are described herein. The disclosed methods, devices, and systems should not be construed as limiting in any way. Instead, the present disclosure is directed toward all novel and nonobvious features and aspects of the various disclosed embodiments, alone and in various combinations and subcombinations with one another. The methods, devices, and systems are not limited to any specific aspect or feature or combination thereof, nor do the disclosed embodiments require that any one or more specific advantages be present or problems be solved.

Although the operations of some of the disclosed methods are described in a particular, sequential order for convenient presentation, it should be understood that this manner of description encompasses rearrangement, unless a particular ordering is required by specific language. For example, operations described sequentially may in some cases be rearranged or performed concurrently. Moreover, for the sake of simplicity, the attached figures may not show the various ways in which the disclosed methods can be used in conjunction with other methods.

As used herein, the term "and/or" used in a list of elements means any one or more of the listed elements. For example, the phrase "A, B, and/or C" means "A," "B," "C," "A and B," "A and C," "B and C" or "A, B and C." As used herein, the term "coupled" generally means physically or electrically linked and does not exclude the presence of intermediate elements between the coupled items absent specific contrary language.

In view of the many possible embodiments to which the principles disclosed herein may be applied, it should be recognized that the illustrated embodiments are only preferred examples and should not be taken as limiting the scope of the disclosure. Rather, the scope of the disclosure is at least as broad as the following claims. We therefore claim all that comes within the scope of these claims.

What is claimed is:

1. A suture clip delivery device comprising:
   a handle having a trigger; and
   an elongated shaft portion; and
   one or more suture clips held within a distal end of the shaft portion, wherein each suture clip comprises two discrete, unconnected, opposing parts;
   wherein the delivery device is configured to attach the one or more suture clips to sutures, one at a time, by compressing the two parts of each suture clip together and causing the two parts to lock together and clamp onto one or more sutures passing between the two parts of the suture clip;
   wherein the delivery device includes two compression members that are configured to apply compression on the two parts of a distal-most suture clip of the one or more suture clips upon actuation of the trigger in order to deploy the distal-most suture clip; and
wherein the two compression members comprise jaws at their distal ends that fit within respective recesses in the two parts of the distal-most suture clip.

2. The delivery device of claim 1, wherein the shaft portion holds a plurality of suture clips and is configured to attach each of the suture clips one-at-a-time to sutures; and after deployment of one of the plurality of suture clips, the delivery device is configured to advance remaining suture clips held in the shaft portion such that a next one of the plurality of suture clips can be deployed by actuating the trigger again.

3. The delivery device of claim 1, wherein for each suture clip held by the delivery device, the two parts of the suture clip are held in a spaced-apart un-engaged configuration, and compression applied by the compression members causes the two parts of the suture clip to engage with each other and become locked together around one or more sutures.

4. The delivery device of claim 1, wherein the two compression members are joined at a pivot joint within the shaft portion.

5. The delivery device of claim 1, further comprising at least two rods within the shaft portion and configured to advance remaining held suture clips after the distal-most suture clip has been deployed.

6. The delivery device of claim 1, wherein the elongated shaft portion is flexible and is configured to be introduced into the heart through a blood vessel from a percutaneous access point.

7. The delivery device of claim 6, wherein a distal end of the device is configured to be introduced into the heart and configured to grasp onto a suture clip already present in the heart and configured to clamp the grasped suture clip onto a suture.

8. The delivery device of claim 6, wherein the shaft portion is steerable and the device includes a proximally controllable actuator to control bending of the distal end of the shaft portion.

9. The delivery device of claim 6, wherein the device includes a light source and an imaging device at a distal end of the shaft portion.

10. The delivery device of claim 1, wherein the elongated shaft portion is malleable.

11. The delivery device of claim 1, wherein the shaft portion comprises four rods within an outer shaft portion, wherein a first two of the rods extend through holes in left-hand parts of the one or more suture clips and a second two of the rods extend through holes in right-hand parts of the one or more suture clips.

12. The delivery device of claim 1, further comprising a pusher rod within the shaft portion that pushes remaining suture clips distally after or when the distal-most suture clip is deployed.

13. The delivery device of claim 1, wherein the shaft portion comprises a slot at a distal end of the shaft portion that is aligned with a gap between the two parts of the distal-most suture clip, such that sutures can be inserted between the two parts by lateral, radial entry through the slot.

14. A suture clip delivery device comprising:
a handle having a trigger; and
an elongated shaft portion; and
one or more suture clips held within a distal end of the shaft portion, wherein each suture clip comprises two discrete, unconnected, opposing parts;
wherein the delivery device is configured to attach the one or more suture clips to sutures, one at a time, by compressing the two parts of each suture clip together and causing the two parts to lock together and clamp onto one or more sutures passing between the two parts of the suture clip;
wherein the delivery device includes two compression members that are configured to apply compression on the two parts of a distal-most suture clip of the one or more suture clips upon actuation of the trigger in order to deploy the distal-most suture clip; and
wherein the shaft portion comprises four rods within an outer shaft portion, wherein a first two of the rods extend through holes in left-hand parts of the one or more suture clips and a second two of the rods extend through holes in right-hand parts of the one or more suture clips.

15. The delivery device of claim 14, wherein the shaft portion holds a plurality of suture clips and is configured to attach each of the suture clips one-at-a-time to sutures; and after deployment of one of the plurality of suture clips, the delivery device is configured to advance remaining suture clips held in the shaft portion such that a next one of the plurality of suture clips can be deployed by actuating the trigger again.

16. The delivery device of claim 14, wherein for each suture clip held by the delivery device, the two parts of the suture clip are held in a spaced-apart un-engaged configuration, and compression applied by the compression members causes the two parts of the suture clip to engage with each other and become locked together around one or more sutures.

17. The delivery device of claim 14, wherein the elongated shaft portion is flexible and is configured to be introduced into the heart through a blood vessel from a percutaneous access point.

18. The delivery device of claim 14, further comprising a pusher rod within the shaft portion that pushes remaining suture clips distally after or when the distal-most suture clip is deployed.

19. The delivery device of claim 14, wherein the shaft portion comprises a slot at a distal end of the shaft portion that is aligned with a gap between the two parts of the distal-most suture clip, such that sutures can be inserted between the two parts by lateral, radial entry through the slot.

20. The delivery device of claim 14, wherein the four rods are spaced apart from one another and are parallel to one another.

* * * * *